(12) United States Patent
Hughes et al.

(10) Patent No.: US 7,708,751 B2
(45) Date of Patent: May 4, 2010

(54) MRI BIOPSY DEVICE

(75) Inventors: Robert J. Hughes, Cincinnati, OH (US); Timothy G. Dietz, Terrace Park, OH (US); Michael J. Andreyko, Cincinnati, OH (US); William E. Clem, Bozeman, MT (US); Martin B. Albini, Bozeman, MT (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1053 days.

(21) Appl. No.: 11/076,612

(22) Filed: Mar. 10, 2005

(65) Prior Publication Data

US 2005/0261581 A1    Nov. 24, 2005

Related U.S. Application Data

(60) Provisional application No. 60/573,510, filed on May 21, 2004.

(51) Int. Cl.
*A61B 17/32* (2006.01)
(52) U.S. Cl. ................ 606/172; 600/550; 600/562
(58) Field of Classification Search .......... 600/550, 600/562; 606/108, 172
See application file for complete search history.

(56) References Cited

U.S. PATENT DOCUMENTS

| | | | |
|---|---|---|---|
| 875,745 A | 12/1907 | Hanes | |
| 4,169,060 A | 9/1979 | Columbus | |
| 4,875,478 A | 10/1989 | Chen | |
| 5,057,085 A | 10/1991 | Kopans | |
| 5,211,165 A | 5/1993 | Dumoulin et al. | |
| 5,307,808 A | 5/1994 | Dumoulin et al. | |
| 5,318,025 A | 6/1994 | Dumoulin et al. | |
| 5,437,277 A | 8/1995 | Dumoulin et al. | |
| 5,443,066 A | 8/1995 | Dumoulin et al. | |
| 5,445,150 A | 8/1995 | Dumoulin et al. | |
| 5,458,112 A | 10/1995 | Weaver | |
| 5,514,131 A | 5/1996 | Edwards et al. | |
| 5,526,822 A | 6/1996 | Burbank et al. | |

(Continued)

FOREIGN PATENT DOCUMENTS

DE     42 16 694     12/1992

(Continued)

OTHER PUBLICATIONS

EnCor™ MRI Specifications and Breast Biopsy System, SenoRx, 2005, pp. 1-2.

(Continued)

*Primary Examiner*—Max Hindenburg
*Assistant Examiner*—Sean P Dougherty

(57) ABSTRACT

A localization mechanism, or fixture, is used in conjunction with a breast coil for breast compression and for guiding a core biopsy instrument during prone biopsy procedures in both open and closed Magnetic Resonance Imaging (MRI) machines. The localization fixture includes a three-dimensional Cartesian positionable guide for supporting and orienting an MRI-compatible biopsy instrument, and in particular a sleeve, to a biopsy site of suspicious tissues or lesions. A depth stop enhances accurate insertion, prevents over-insertion or inadvertent retraction of the sleeve. The sleeve receives a probe of the MRI-compatible biopsy instrument and may contain various features to enhance its imagability, to enhance vacuum and pressure assist therethrough, etc.

29 Claims, 38 Drawing Sheets

U.S. PATENT DOCUMENTS

| | | | |
|---|---|---|---|
| 5,531,703 | A | 7/1996 | Skwarek et al. |
| 5,541,972 | A | 7/1996 | Anthony |
| 5,560,373 | A * | 10/1996 | De Santis ............... 600/566 |
| 5,611,352 | A | 3/1997 | Kobren et al. |
| 5,678,549 | A | 10/1997 | Heywang-Koebrunner et al. |
| 5,715,822 | A | 2/1998 | Watkins et al. |
| 5,775,333 | A | 7/1998 | Burbank et al. |
| 5,782,764 | A | 7/1998 | Werne |
| 5,800,389 | A | 9/1998 | Burney et al. |
| 5,827,305 | A | 10/1998 | Gordon |
| 5,830,219 | A | 11/1998 | Bird et al. |
| 5,855,554 | A | 1/1999 | Schneider et al. |
| 5,882,305 | A | 3/1999 | Dumoulin et al. |
| 5,913,863 | A | 6/1999 | Fischer et al. |
| 5,921,943 | A | 7/1999 | Kass |
| 5,954,670 | A | 9/1999 | Baker |
| 6,022,325 | A | 2/2000 | Siczek et al. |
| 6,036,632 | A | 3/2000 | Whitmore, III et al. |
| 6,048,321 | A | 4/2000 | McPherson et al. |
| 6,077,230 | A | 6/2000 | Gregoire et al. |
| 6,083,177 | A * | 7/2000 | Kobren et al. ............ 600/564 |
| 6,086,544 | A | 7/2000 | Hibner et al. |
| 6,142,955 | A * | 11/2000 | Farascioni et al. ........ 600/562 |
| 6,165,137 | A | 12/2000 | Milliman et al. |
| 6,174,291 | B1 | 1/2001 | McMahon et al. |
| 6,192,583 | B1 | 2/2001 | Roffelsen |
| 6,203,524 | B1 | 3/2001 | Burney et al. |
| 6,261,241 | B1 | 7/2001 | Burbank et al. |
| 6,261,243 | B1 | 7/2001 | Burney et al. |
| 6,264,670 | B1 | 7/2001 | Chin |
| 6,270,506 | B1 * | 8/2001 | Sittek et al. ............... 606/130 |
| 6,272,372 | B1 | 8/2001 | Fisher |
| 6,289,233 | B1 | 9/2001 | Dumoulin et al. |
| 6,321,613 | B1 | 11/2001 | Avidor |
| 6,416,510 | B1 | 7/2002 | Altman et al. |
| 6,428,498 | B2 | 8/2002 | Uflacker |
| 6,432,064 | B1 | 8/2002 | Hibner et al. |
| 6,447,477 | B2 | 9/2002 | Burney et al. |
| 6,471,700 | B1 | 10/2002 | Burbank et al. |
| 6,558,337 | B2 | 5/2003 | Dvorak et al. |
| 6,626,849 | B2 | 9/2003 | Huitema et al. |
| 6,638,235 | B2 | 10/2003 | Miller et al. |
| 6,659,338 | B1 | 12/2003 | Dittmann et al. |
| 6,675,037 | B1 | 1/2004 | Tsekos |
| 6,752,768 | B2 | 6/2004 | Burdorff et al. |
| 6,758,824 | B1 | 7/2004 | Miller et al. |
| 6,758,848 | B2 | 7/2004 | Burbank et al. |
| 6,770,063 | B2 | 8/2004 | Goldberg et al. |
| 6,846,320 | B2 | 1/2005 | Ashby et al. |
| 6,863,676 | B2 | 3/2005 | Lee et al. |
| 6,889,073 | B2 | 5/2005 | Lampman et al. |
| 6,975,701 | B2 | 12/2005 | Galkin |
| 6,999,553 | B2 | 2/2006 | Livingston |
| 7,160,292 | B2 | 1/2007 | Moorman et al. |
| 7,171,256 | B1 | 1/2007 | Graessle et al. |
| 7,276,032 | B2 | 10/2007 | Hibner |
| 7,347,829 | B2 | 3/2008 | Mark et al. |
| 7,351,228 | B2 | 4/2008 | Keane et al. |
| 7,470,237 | B2 * | 12/2008 | Beckman et al. .......... 600/564 |
| 2001/0049502 | A1 | 12/2001 | Chen |
| 2003/0004529 | A1 | 1/2003 | Tsonton et al. |
| 2003/0023239 | A1 | 1/2003 | Burbank et al. |
| 2003/0109802 | A1 | 6/2003 | Laseke et al. |
| 2003/0109803 | A1 | 6/2003 | Huitema et al. |
| 2003/0199753 | A1 | 10/2003 | Hibner et al. |
| 2003/0199754 | A1 | 10/2003 | Hibner et al. |
| 2003/0199785 | A1 | 10/2003 | Hibner et al. |
| 2004/0006347 | A1 | 1/2004 | Sproul |
| 2004/0077938 | A1 | 4/2004 | Mark et al. |
| 2004/0077972 | A1 | 4/2004 | Tsonton et al. |
| 2004/0210161 | A1 | 10/2004 | Burdorff et al. |
| 2004/0230157 | A1 | 11/2004 | Perry et al. |
| 2006/0004258 | A1 | 1/2006 | Sun et al. |
| 2008/0161720 | A1 | 7/2008 | Nicoson et al. |
| 2008/0200834 | A1 | 8/2008 | Mark et al. |

FOREIGN PATENT DOCUMENTS

| | | |
|---|---|---|
| EP | 0 995 400 | 4/2000 |
| EP | 1 410 764 | 4/2004 |
| EP | 1598006 | 11/2005 |
| EP | 1598015 | 11/2005 |
| FR | 2 332 743 | 6/1977 |
| GB | 92 06 853.7 | 10/1992 |
| WO | WO 93/17620 | 9/1993 |
| WO | WO 96/14023 | 5/1996 |
| WO | WO 98/22022 | 5/1998 |
| WO | WO 02/13709 | 2/2002 |
| WO | WO 03/026509 | 4/2003 |
| WO | WO 2005/017775 | 2/2005 |

OTHER PUBLICATIONS

European Search Report, dated Jan. 5, 2004 for EPO Application No. 03252518.0.

Noras Medizintechnik, Operator Manual, Model MR-B1 160, Revision 3, pp. 1-11.

EPO Search Report, Application No. 07250438.4, May 21, 2007, pp. 1-5.

European Search Report dated Sep. 25, 2007 for Application No. 07252089.3.

European Search Report for EP 05 254 3171, Sep. 23, 2005, pp. 1-5.

International Search Report for PCT/US2005/017775, May 21, 2004, pp. 1-4.

U.S. Appl. No. 60/573,510, filed May 21, 2004, Hughes et al.

U.S. Appl. No. 11/025,556, filed Dec. 29, 2004, Hibner et al.

U.S. Appl. No. 11/103,718, filed Apr. 12, 2005, Tsonton et al.

U.S. Appl. No. 11/103,959, filed Apr. 12, 2005, Hughes et al.

European Search Report dated Sep. 14, 2005 for Application No. EP 05253171.

European Search Report dated Sep. 20, 2005 for Application No. PCT/US2005/017775.

European Search Report dated May 21, 2007 for Application No. 07250438.4.

Office Action dated Jul. 1, 2008 for U.S. Appl. No. 11/463,346.

Office Action dated Mar. 21, 2008 for U.S. Appl. No. 11/103,718.

Office Action dated Apr. 4, 2008 for U.S. Appl. No. 11/103,959.

Office Action dated May 23, 2008 for Chinese Application No. 200510074636.1.

Heywant-Köbrunner et al., "MR-guided percutaneous excisional and incisional biopsy of breast lesions," Eur. Radiol., vol. 9 (1999) pp. 1656-1665.

Savitz, M.H., "CT-Guided Needle Procedures for Brain Lesions: 20 Years' Experience," The Mount Sinai Journal of Medicine, vo. 67(4) (Sep. 2000) pp. 318-321.

Savitz, M.H., "Free-hand CT-guided Needle for Biopsy and Drainage of Intracerebral Lesions. Ten Years Experience," Int. Surg., vol. 77 (1992) pp. 211-215.

Preliminary Patentability Report dated Nov. 21, 2006 for Application No. PCT/US2005/017775.

Written Opinion dated Sep. 29, 2005 for Application No. PCT/US2005/017775.

Perlot, C. et al., "Multicenter study for the evaluation of a dedicated biopsy device for MR-guided vacuum biopsy of the breast," Eur. Radiol. , vol. 12 (2002) pp. 1463-1470.

Viehweg, P. et al., "MR-guided interventional breast procedures considering vacuum biopsy in particular," Eur. J. of Radiol., vol. 42 (2002) pp. 32-39.

Daniel, B.L. et al., "An MRI-Compatible Semiautomated Vacuum-Assisted Breast Biopsy System: Initial Feasibility Study," J. of Magnetic Resonance Imaging, vol. 21 (2005) pp. 637-644.

Kuhl, C.K. et al., "Interventional Breast MR Imaging: Clinical Use of a Stereotactic Localization and Biopsy Device," Radiology, vol. 204 (1997) pp. 667-675.

* cited by examiner

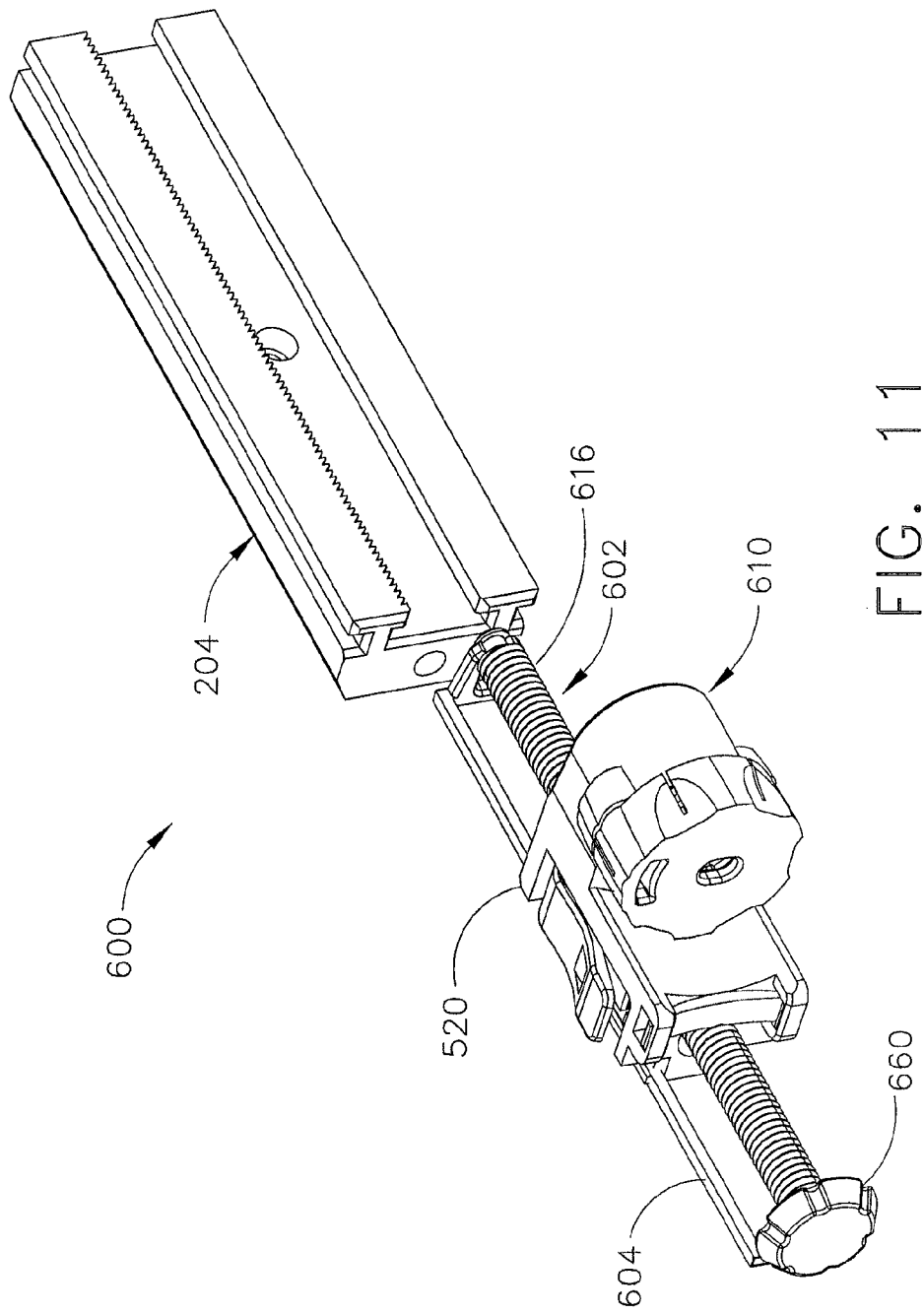

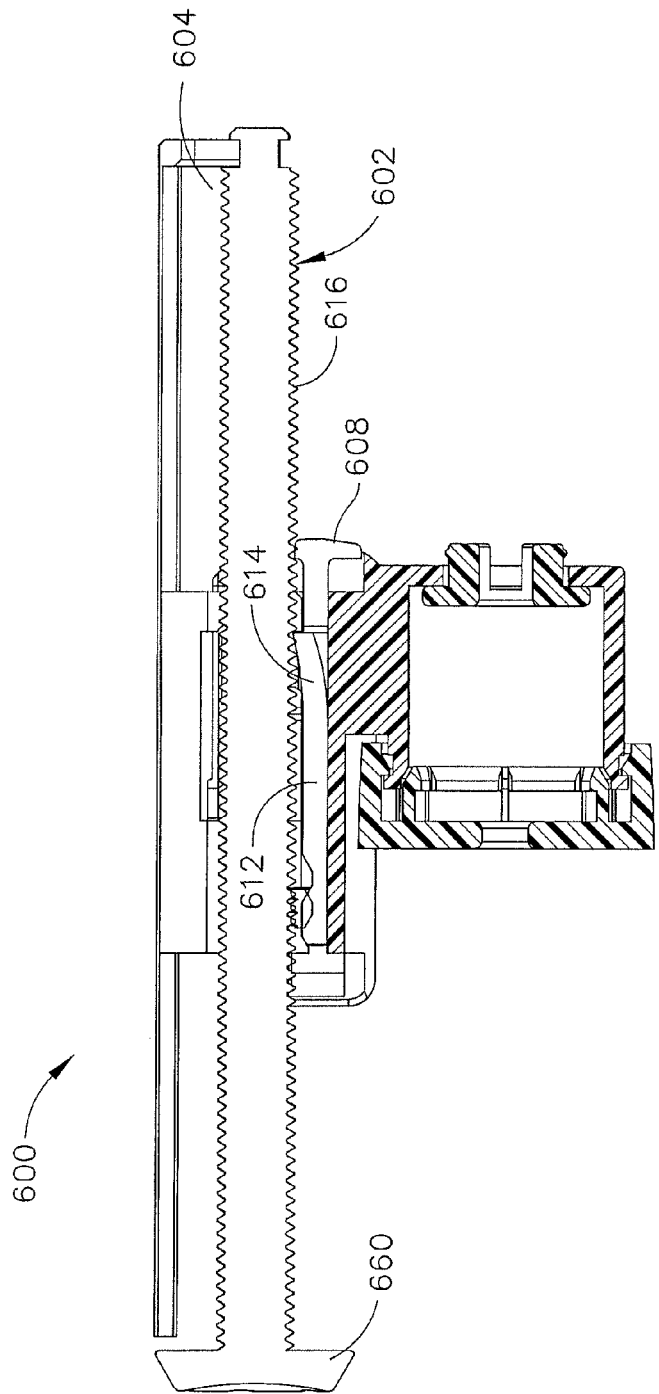

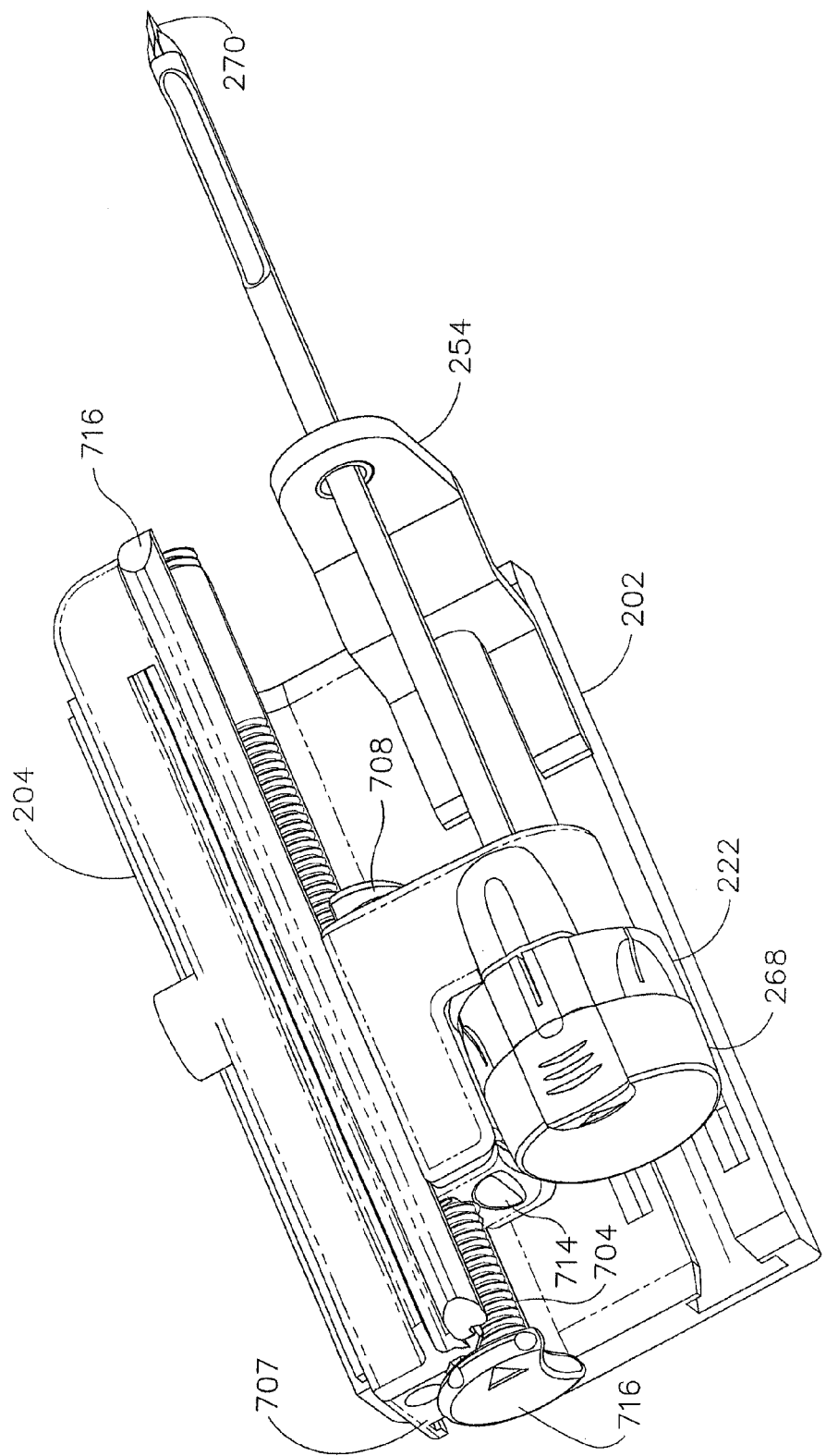

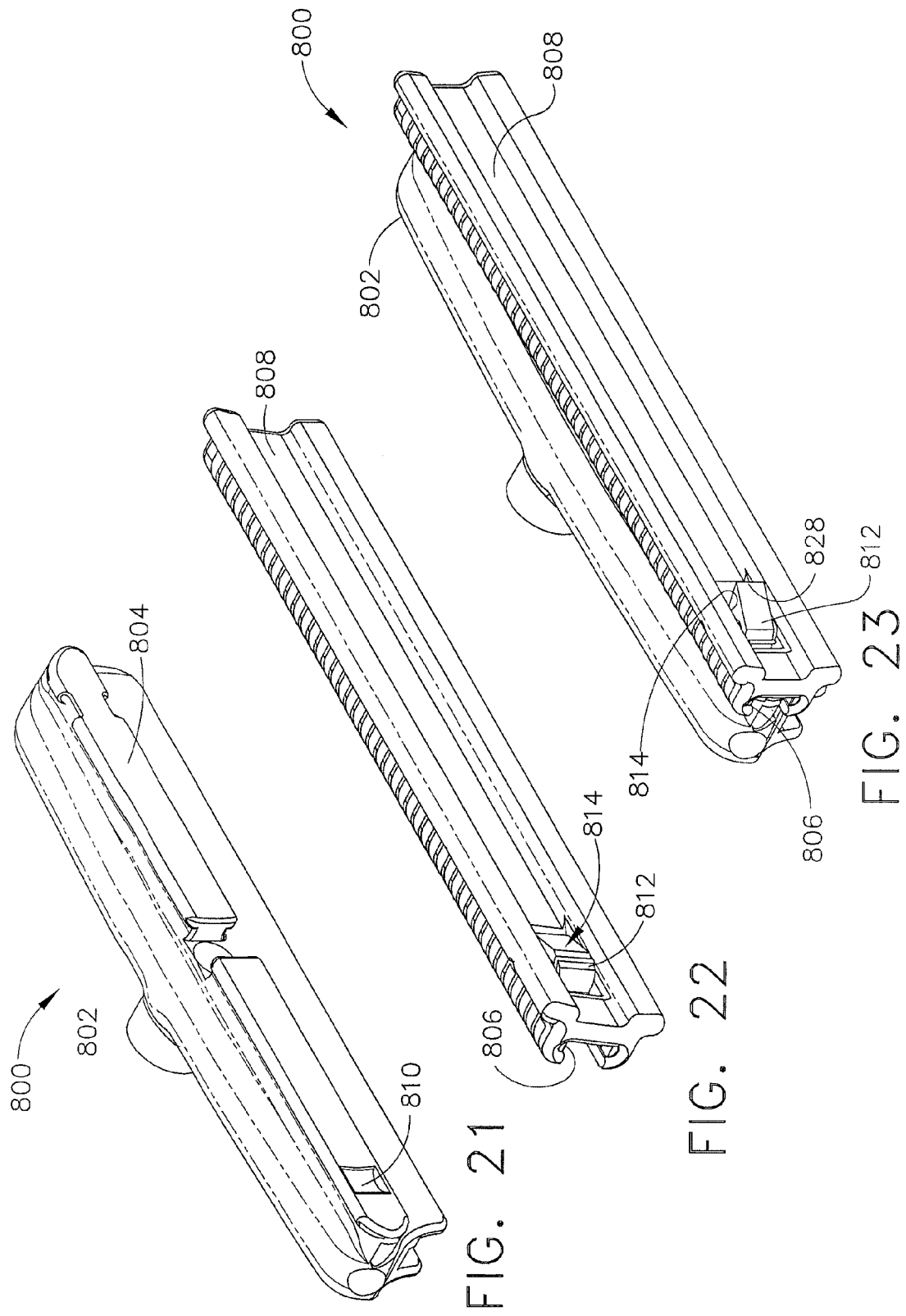

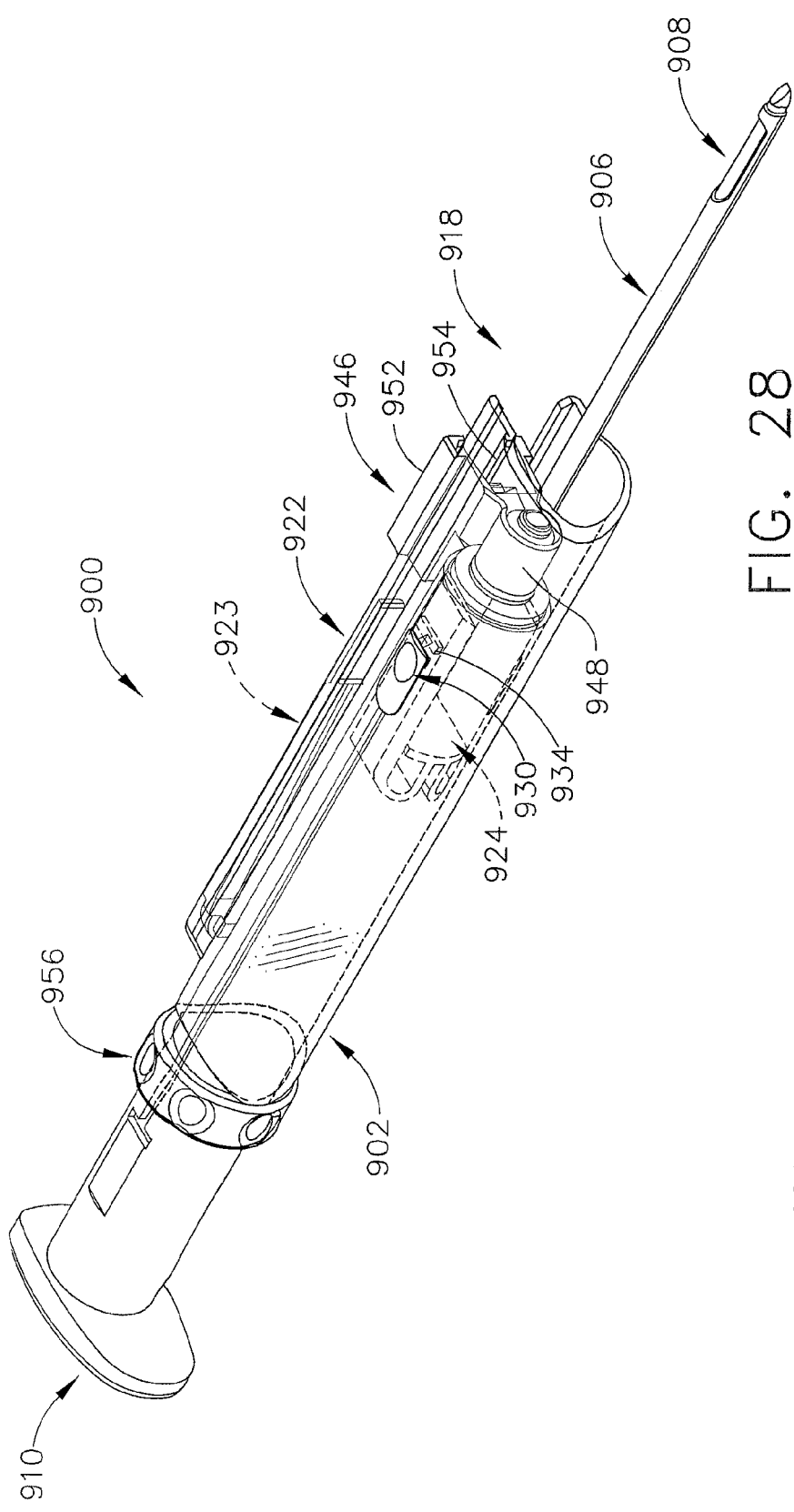
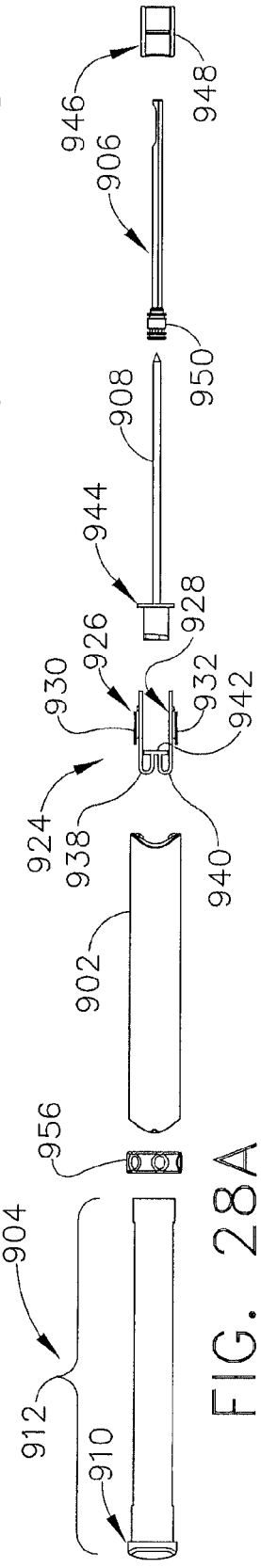
FIG. 28
FIG. 28A

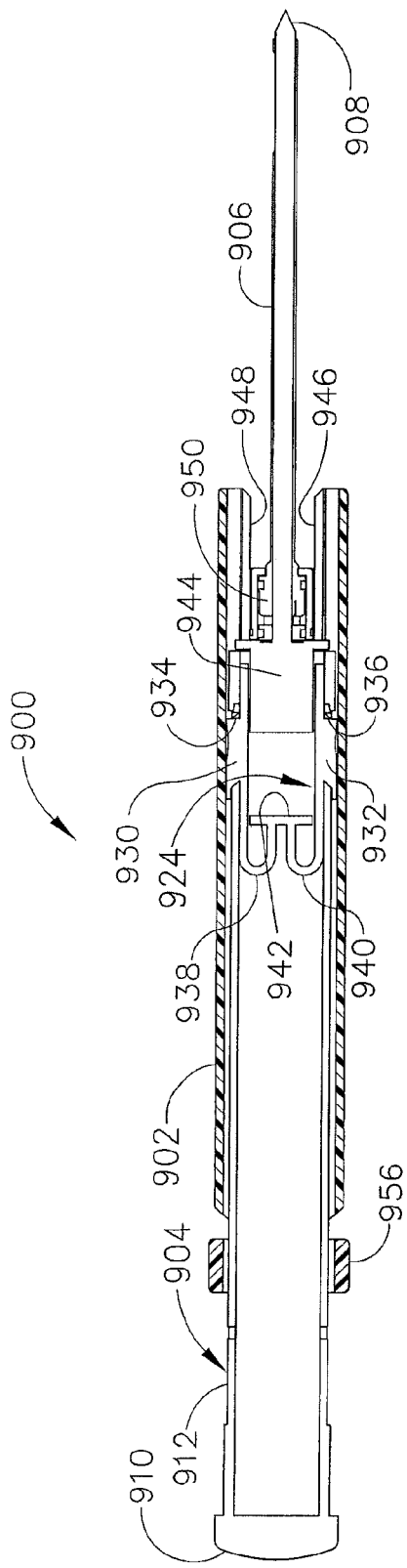
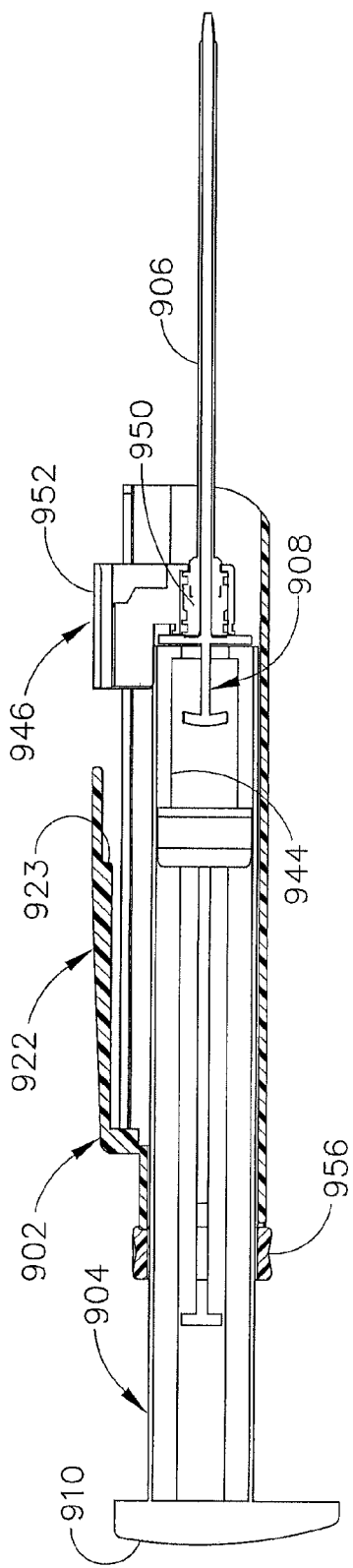
FIG. 28B
FIG. 28C

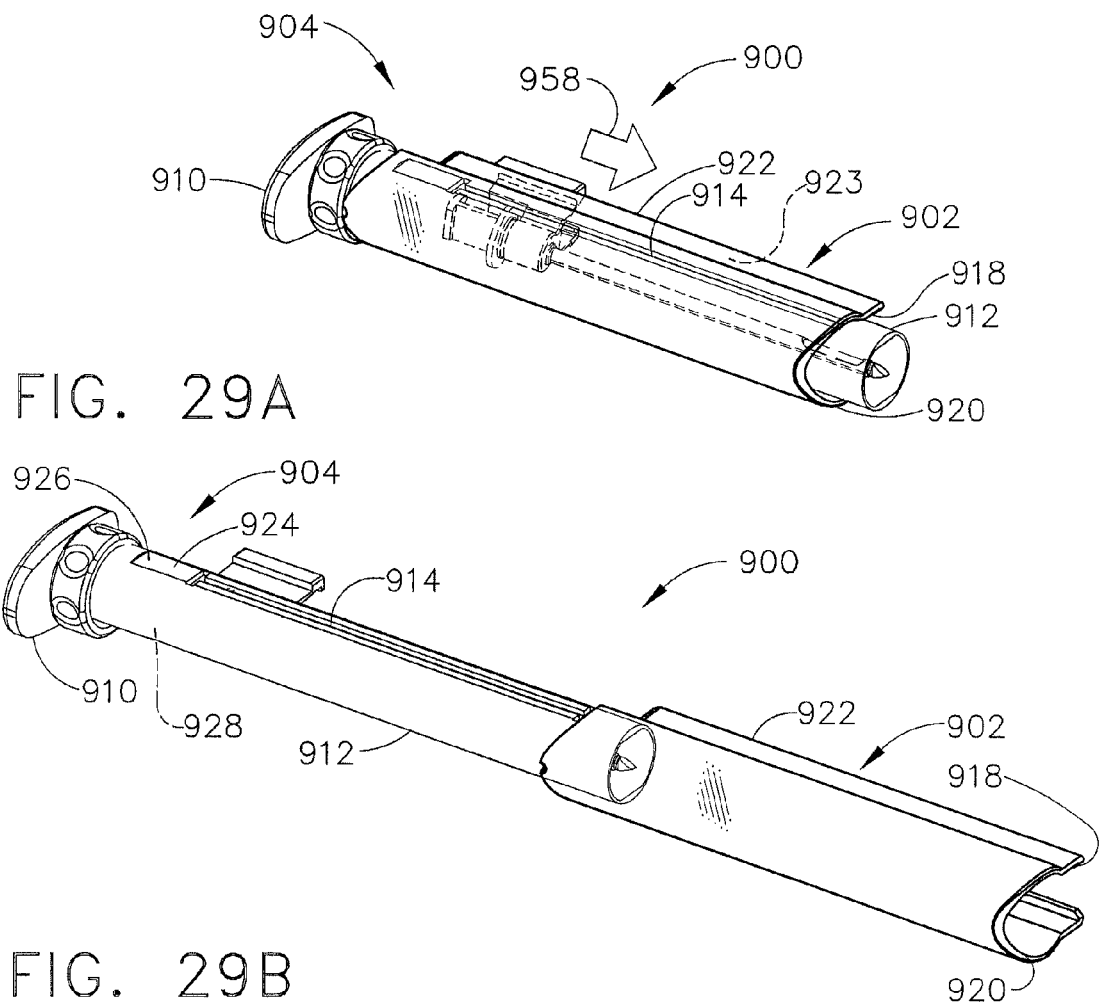
FIG. 29A
FIG. 29B
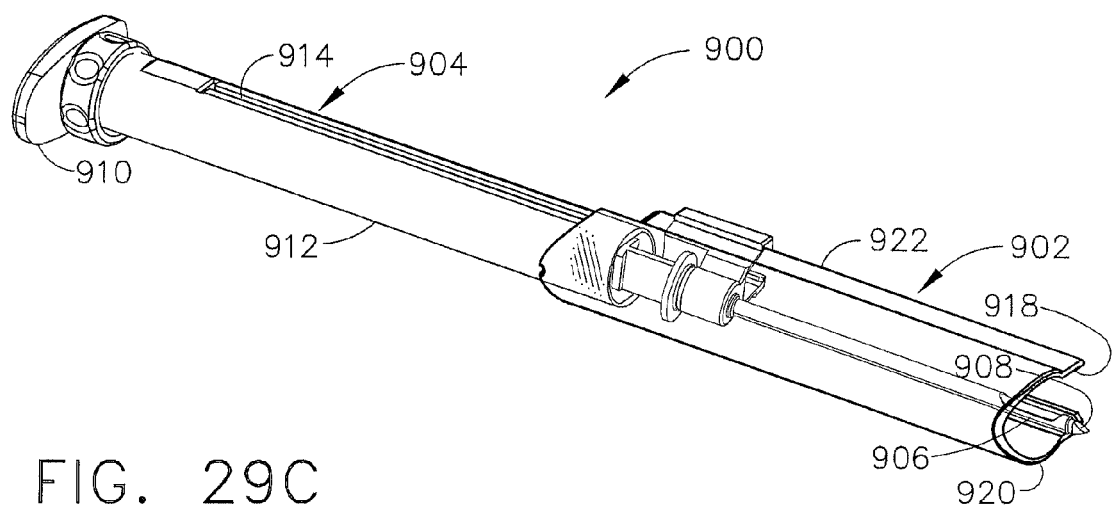
FIG. 29C

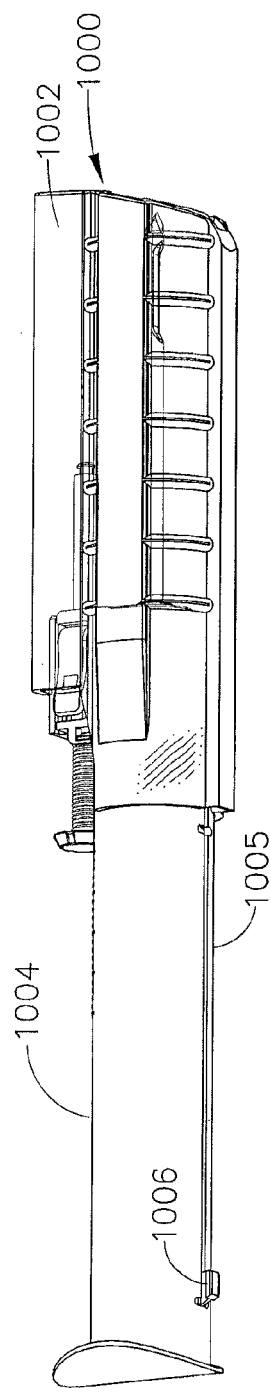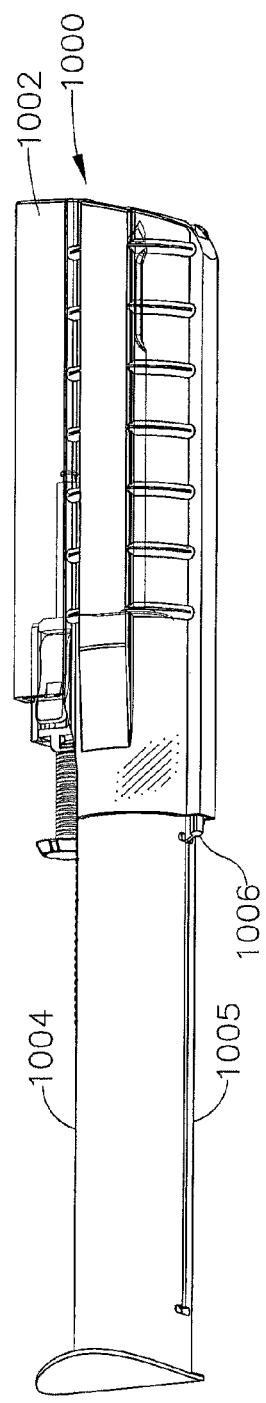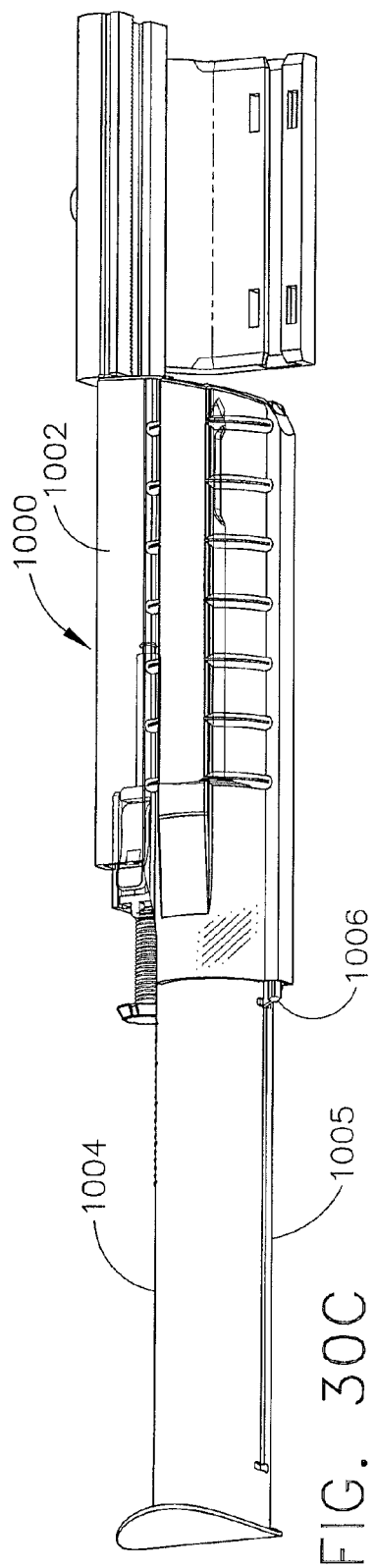

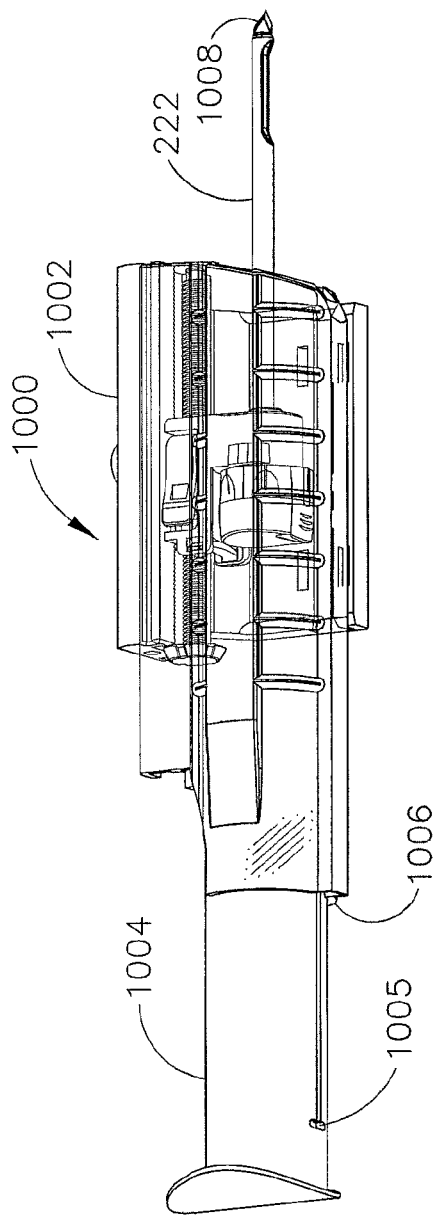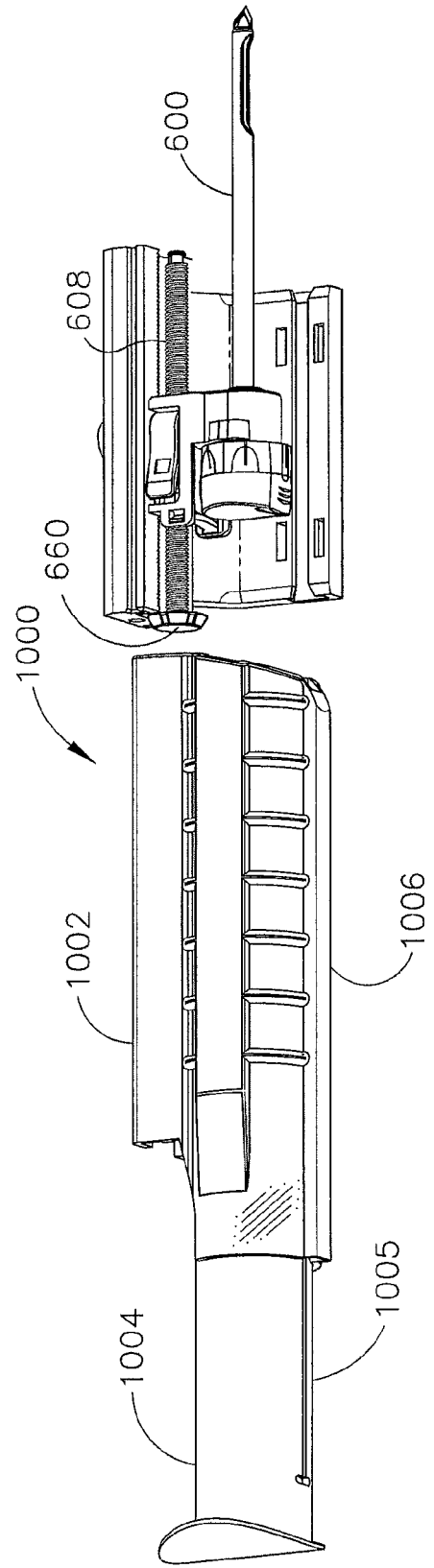
FIG. 30D
FIG. 30E

MRI BIOPSY DEVICE

CROSS REFERENCE TO RELATED APPLICATIONS

The present application claims the benefit of U.S. provisional patent application entitled "MRI BIOPSY DEVICE" to Hughes et al., Ser. No. 60/573,510, filed on 21 May 2004 and is related to the nonprovisional patent application entitled "LOCALIZATION MECHANISM FOR AN MRI COMPATIBLE BIOPSY DEVICE" to Hibner et al., Ser. No. 10/171,330, filed on 23 Apr. 2002, and published on 23 Oct. 2003 as Pub. No. US 2003/0199785, the disclosure of both are hereby incorporated by reference in their entirety.

FIELD OF THE INVENTION

The present invention relates, in general, to a method of imaging assisted tissue sampling and, more particularly, to an improved method for positioning a biopsy probe with respect to a magnetic resonance imaging (MRI) breast coil for acquiring subcutaneous biopsies and for removing lesions.

BACKGROUND OF THE INVENTION

Recently, core biopsy devices have been combined with imaging technology to better target a lesion in breast tissues. One such commercially available product is marketed under the trademark name MAMMOTOME™, by Ethicon Endo-Surgery, Inc. An embodiment of such a device is described in U.S. Pat. No. 5,526,822 issued to Burbank, et al., on Jun. 18, 1996, and is hereby incorporated herein by reference. Its handle receives mechanical and electrical power as well as vacuum assist from a remotely positioned control module that is spaced away from the high magnetic field of a Magnetic Resonance Imaging (MRI) machine.

As seen from that reference, the instrument is a type of image-guided, percutaneous coring, breast biopsy instrument. It is vacuum-assisted, and some of the steps for retrieving the tissue samples have been automated. The physician uses this device to capture "actively" (using the vacuum) the tissue prior to severing it from the body. This allows the sampling of tissues of varying hardness. In addition, a side opening aperture is used, avoiding having to thrust into a lesion, which may tend to push the mass away, cause a track metastasis, or cause a hematoma that, with residual contrast agent circulating therein, may mimic enhancement in a suspicious lesion. The side aperture may be rotated about a longitudinal axis of the probe, thereby allowing multiple tissue samples without having to otherwise reposition the probe. These features allow for substantial sampling of large lesions and complete removal of small ones.

In the aforementioned Pub. No. US 2003/0199785 to Hibner et al., localization fixtures are described that are attachable to a breast coil. These localization fixtures aid in accurately positioning the probe to a location of a suspicious lesion within breast tissue. In particular, the X-Y-Z Cartesian coordinates of a suspicious lesion are referenced to a fiduciary marker in the localization fixture. Humanly visible measurement guides for each axis then allow the probe to be correspondingly positioned after a patient has been withdrawn from a closed bore MRI machine without the need for imaging the probe during insertion. In addition, the localization fixture enables use of a detachable probe of an MRI biopsy device. Thus, during subsequent reimaging of the probe, a handle of the MRI biopsy device may be detached, as may be necessary within the close confines of a closed bore MRI machine. When the handle is attached to the probe, various support structures of the localization fixture are described that support the extended length of the handle.

While a localization fixture used with a detachable MRI biopsy probe has a number of advantages, it would be desirable to incorporate additional features that further assist in accurately positioning the probe, preventing over insertion or inadvertent retraction of the probe, and supporting the MRI biopsy device.

Consequently, a significant need exists for an improved localization fixture for in an MRI guided biopsy procedure that assists in locating a suspicious lesion and for accurately performing a biopsy or complete removal of the suspicious lesion, even in conjunction with the close confines of closed bore MRI machines.

BRIEF SUMMARY OF THE INVENTION

The invention overcomes the above-noted and other deficiencies of the prior art by providing a localization and guidance assembly that interfaces an MRI biopsy device to a breast coil to accurately position and maintain a probe at a desired position in a patient's breast for performing biopsy and related diagnostic and therapeutic procedures, and especially for making a single insertion and taking multiple biopsy samples.

In one aspect of the invention, a guide element is selectively positioned parallel to a desired axis of penetration into a patient. A mount movingly engages the guide element so that a penetrating portion of a biopsy instrument is supported along the axis of penetration during insertion into the patient. A depth limiting member, attached to a selected one of the mount and guide element, is advantageously adjusted prior to full insertion to arrest distal movement of the mount when the penetrating portion reaches a desired depth.

In another aspect of the invention, a localization fixture compressively localizes a patient's breast, while a pedestal is laterally positioned to support the guide element, which is also vertically adjusted on the pedestal into parallel alignment with the desired axis of penetration. Thereby, accurate insertion and greater hands free maintenance of position is achieved for breast biopsy procedures.

In yet another aspect of the invention, a method of guiding a penetrating portion of a biopsy device includes aligning a guide element parallel to and offset from a designated axis of penetration into a patient. Setting a depth limit for penetration prior to penetrating tissue assures that overshooting the intended target is avoided. Then slidingly engaging the penetrating portion of the biopsy device to the guide element effects penetration of the patient along the designated axis of penetration until arrested by the depth limit setting.

The present invention shall be made apparent from the accompanying wings and the description thereof.

DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 11 is a top, proximal and right perspective view of another depth guidance assembly having rough adjust and release buttons shown detached from a primary targeting rail for the MRI biopsy system of FIG. 1;

FIG. 13A is a top view of the depth guidance assembly of FIG. 13 taken in cross section along lines 13A-13A;

FIG. 18 is a top, proximal and right perspective view of the telescoping depth guidance assembly of FIG. 17 after unscrewing the depth stop second rail;

FIG. 21 is a top, proximal and right perspective view of an alternative primary targeting rail including a pawl recess for the MRI biopsy system of FIG. 1;

FIG. 22 is a perspective view of an alternative intermediate telescoping rail with a pawl in a second position;

FIG. 23 is a perspective view of the alternative intermediate telescoping rail of FIG. 22, with a pawl in a third position, attached to the primary targeting rail of FIG. 21;

FIG. 28 is a perspective view of a laterally guided biopsy cassette for the MRI biopsy system of FIG. 1;

FIG. 29 is a left side view in elevation of a disassembled laterally guided biopsy cassette of FIG. 28;

FIG. 28B is a left side view in elevation of the laterally guided biopsy cassette of FIG. 28 taken along a longitudinal centerline;

FIG. 28C is a top view of the laterally guided biopsy cassette of FIG. 28 taken along the longitudinal centerline;

FIG. 29A is a perspective view of the laterally guided biopsy cassette of FIG. 28 in an initial condition with the glide sleeve retracted over the plunger handle;

FIG. 29B is a perspective view of the laterally guided biopsy cassette of FIG. 29A after distally advancing the glide sleeve from the plunger handle;

FIG. 29C is a perspective view of the laterally guided biopsy cassette of FIG. 29B after depressing the release buttons and advancing a sleeve and obturator out of a plunger tube but within the confines of the glide sleeve;

FIG. 30A is a perspective view of an alternative biopsy cassette containing the depth guidance assembly with rough adjust and release buttons of FIG. 11 with a sleeve mounted thereto and an obturator retracted into a plunge tube of the alternative biopsy cassette;

FIG. 30B is a perspective view of the alternative biopsy cassette of FIG. 30A after a slide control is advanced on the plunge tube to insert the obturator into the sleeve;

FIG. 30C is a perspective view of the alternative biopsy cassette being engaged onto a targeting rail and cassette of a localization fixture;

FIG. 30D is a perspective view of the alternative biopsy cassette fully engaged onto the targeting rail and cassette of a localization fixture; and FIG. 30E is a perspective of the alternative biopsy cassette removed from the targeting rail and cassette of a localization fixture leaving the depth guidance assembly thereon.

DETAILED DESCRIPTION OF THE INVENTION

Figure 1:
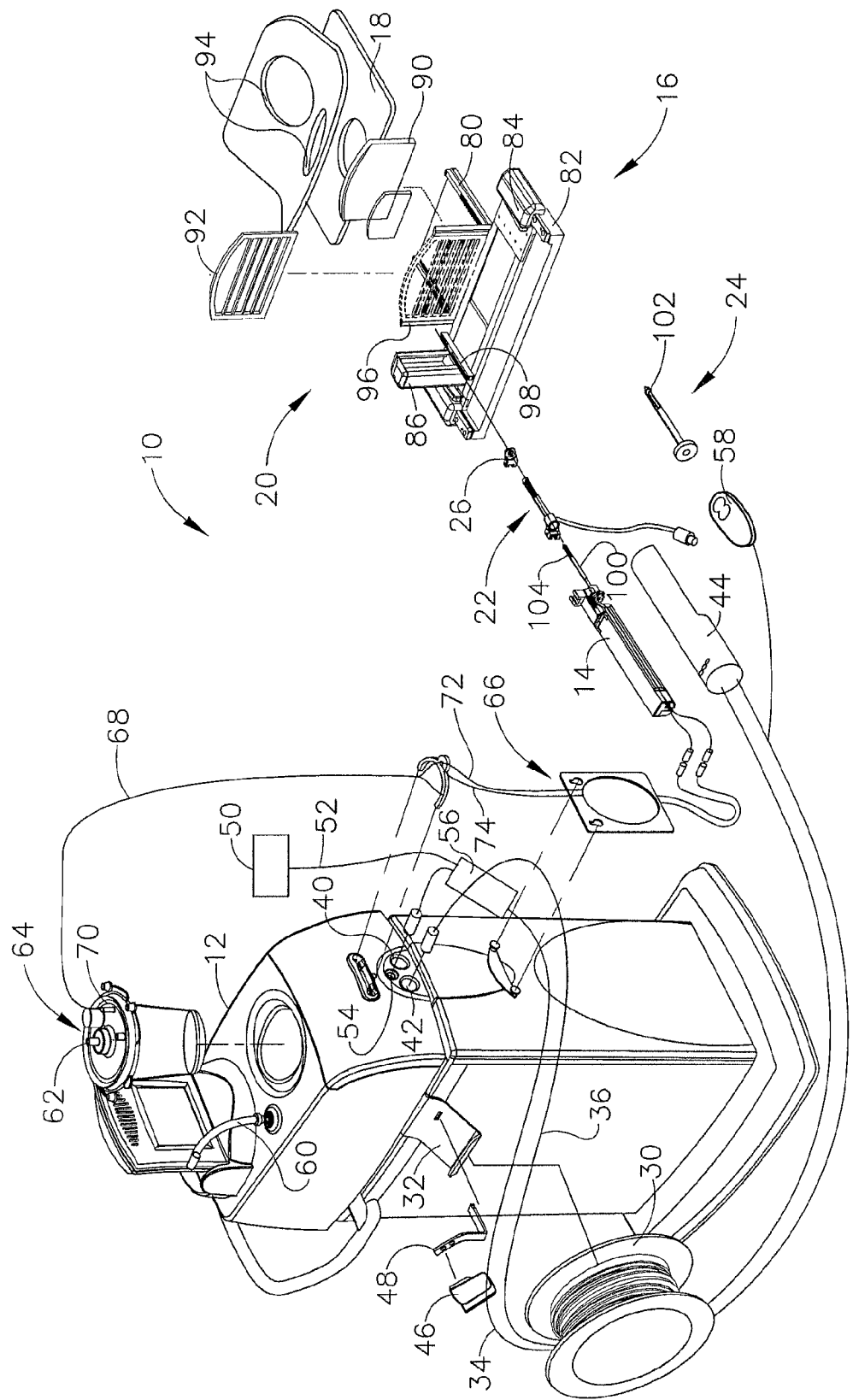
FIG. 1 is a perspective disassembled view of a Magnetic Resonance Imaging (MRI) biopsy system incorporating an elemental version of a guidance apparatus including a single targeting rail for positioning a probe depth-stop and guiding a biopsy device.

Turning to the Drawings, wherein like numerals denote like components throughout the several views, in FIG. 1, a Magnetic Resonance Imaging (MRI) biopsy system 10 includes a guide element and an adjustable depth stop that assists a surgeon in inserting a biopsy probe along a desired trajectory without overshooting. In particular, a guide element is adjustably positioned to be parallel to an axis of penetration, which in turn is aimed to pass through an insertion point to a surgical site inside of the patient, typically where a suspicious lesion has been imaged. With a biopsy device detached from the guide element, a depth stop is adjustably set to a desired penetration depth. Then a mount that supports at least the penetrating portion of the biopsy device is guided by the guide element as tissue of the patient is penetrated until the depth stop arrests further movement of the mount relative to the guide element. Thereby, accurate insertion of the penetrating portion without overshooting is enabled.

The MRI biopsy system 10 includes a control module 12 that typically is placed outside of a shielded room containing an MRI machine (not shown) or at least spaced away to mitigate detrimental interaction with its strong magnetic field and/or sensitive radio frequency (RF) signal detection antennas. The control module 12 controls and powers an MRI biopsy device 14 that is compatible for use in close proximity to the MRI machine. An example of an MRI biopsy device 14 is the afore-mentioned MAMMOTOME™ instrument. The MRI biopsy device 14 is accurately positioned by a localization fixture 16 that is attached to a breast coil 18, which in turn supports a patient (not shown). Examples of commercially available breast coils 18 include the BIOPSY BREAST COIL MODEL BBC by MRI DEVICES CORPORATION of Waukesha Wis. A guidance assembly 20, and in particular a sleeve 22, advantageously attaches to the localization fixture 16 to increase imaging and therapeutic flexibility and accuracy in conjunction with selective use of the MRI biopsy device 14 at particular parts of the procedure. The guidance assembly 20 may include one or more obturators 24 with one depicted that seals the sleeve 22 during insertion and during subsequent portions of the procedure in which the MRI biopsy device 14 is not inserted therein. A depth stop 26 is provided for use with the localization fixture 16 to advantageously prevent over-insertion of the sleeve 22, inadvertent retraction of the sleeve 22 and/or to enhance accurate placement of the sleeve 22 to a desired location along the Z-Axis.

For convenience, herein a convention is used for locating a suspicious lesion by Cartesian coordinates within breast tissue referenced to the localization fixture 16 and to thereafter position an instrument (e.g., sleeve 22) to this location without necessarily continuously imaging the region. As will be described in greater detail below, a perforated barrier that is compressed along an outside side of the breast, with respect to a medial plane of the chest of the patient, defines an X-Y plane, with the X-axis being vertical (sagittal) with respect to a standing patient and which corresponds to a left to right axis as viewed by a clinician facing the externally exposed portion of the localization fixture 16. A fiduciary marker (not shown) attached to or positioned relative to the localization fixture 16 proximate to the patient's skin defines the origin of this plane. Perpendicular to this X-Y plane extending toward the medial side of the breast is the Z-axis, which typically corresponds to the orientation and depth of insertion of the MRI biopsy device 14, although it should be appreciated that variations may allow insertion at an angle to this Z-axis. Thus, for clarity, the term Z-axis may be used interchangeably with "axis of penetration", although the latter may or may not be orthogonal to the spatial coordinates used to locate an insertion point on the patient.

Separating the tracking rail that supports a mount/depth stop from a biopsy rail that supports the weight of the biopsy device advantageously reduces interference between the various components, allowing a sequence of operation wherein certain components may be selectively installed and removed without interfering with other components.

In use, the MRI biopsy system 10 is prepared for use by placing a cable management spool 30 upon a cable management attachment saddle 32 that projects from a side of the control module 12. Wound upon the cable management spool 30 is a paired electrical cable 34 and mechanical cable 36 for communicating control signals and cutter rotation/advancement motions respectively. In particular, electrical and mechanical cables 34, 36 each have one end connected to respective electrical and mechanical ports 40, 42 in the control module 12 and another end connected to a holster 44 that receives the MRI biopsy device 14. An MRI docking cup 46, which may hold the holster 44 when not in use, is hooked to the control module 12 by a docking station mounting bracket 48.

An interface lock box 50 mounted to a wall provides a tether 52 to a lockout port 54 on the control module 12. The tether 52 is advantageously uniquely terminated and of short length to preclude inadvertent positioning of the control module 12 too close to the MRI machine. An in-line enclosure 56 may advantageously register the tether 52, electrical cable 34 and mechanical cable 36 to their respective ports 54, 42, 44 on the control module 12. A remote keypad 58 may be distally connected to the electrical cable 34 to enhance clinician control of the MRI biopsy device 14, especially when controls on the MRI biopsy device 14 itself are not readily accessible after insertion into the localization fixture 16.

Vacuum assist is provided by a first vacuum line 60 that connects between the control module 12 and an outlet port 62 of a vacuum canister 64 that catches liquid and solid debris. A tubing kit 66 completes the pneumatic communication between the control module 12 and the MRI biopsy device 14. In particular, a second vacuum line 68 is connected to an inlet port 70 of the vacuum canister 64. The second vacuum line 68 divides into two vacuum lines 72, 74 that are attached to the MRI biopsy device 14. With the MRI biopsy device 14 installed in the holster 44, the control module 12 performs a functional check. Saline is manually injected into biopsy device 14 to serve as a lubricant and to assist in achieving a vacuum seal. The control module 12 actuates a cutter mechanism (not shown) in the MRI biopsy device 14, monitoring full travel.

The portion of the MRI biopsy system 10 used near the MRI machine is also assembled. The generally known breast coil 18 is placed upon a gantry of the MRI machine, along with other body support pads (not shown). The localization fixture 16, which is attached within a recess on either lateral side of the breast coil 18 to access a patient's breast that is pendulously exposed therein, includes a horizontal medial plate 80, a reusable base assembly 82, a lateral assembly 84, and a positioning pedestal 86. The localization fixture 16 is also assembled with a disposable medial fence 90 and a lateral window (or perforated plate) 92.

The base assembly 82 is placed within a selected lateral recess of the breast coil 18. The medial fence 90 attaches to a medial edge of the medial plate 80, aligned vertically approximately along a longitudinal axis of the breast coil 18 under an inner edge of a selected breast aperture 94 that receives a patient's breast. With the patient thus positioned and the outer area of the breast sterilized, the lateral window 92 is downwardly slid into a three-sided frame guide 96 of the lateral assembly 84, which in turn is placed upon the medical plate 80. The base assembly 82 and lateral assembly 84 are moved with respect to one another along the Z-axis to compress the patient's breast between the medial fence 90 and the lateral window 92. A mechanism formed between the lateral assembly 84, base assembly 82, and medial plate 80 maintains this compression.

Contrast agent may be injected into the patient to enhance the imaging. The gantry is advanced into the MRI machine bore to image the localization fixture 16 and breast tissue. The fiduciary marker on the lateral window 92 is located and designated as the origin of the X-Y-Z coordinates. Then a suspicious lesion is located within the image and a point thereon selected to determine its location relative to the origin. It should be appreciated that orienting the X-Y-Z axis of an initial scan may be facilitated by having the lateral window 92 formed of an imagable material, thus presenting an X-Y plane in addition to the origin point of the fiduciary marker. With the target location determined, the gantry is withdrawn from the MRI machine bore.

The positioning pedestal 86 is slidably engaged along the X-axis of the lateral assembly 84 and defines a vertical guide for positioning a single targeting rail ("track") 98 at a selected Y-axis coordinate. The track 98 in turn provides a depth guide along the Z-axis for positioning the depth stop 26 and the holster 44 at a desired Z-axis coordinate. The depth stop 26 is latched onto the track 98. Thereafter, a marking instrument (not shown) may be inserted through the depth stop 26 to mark the insertion point on the breast. Thereafter, the depth stop 26 is moved out of the way. Anesthesia is injected superficially, following by a scoring cut at the marked location and a subsequent injection of anesthesia more deeply into the scored cut. The depth stop 26 is then repositioned on the track 98 to the desired Z-axis coordinate reference.

The obturator 24 is inserted into the sleeve and may be positioned to close any apertures of the sleeve 22 (side and/or distal end) to present a closed surface to the breast tissue. The obturator may also be shaped or formed to enhance the visibility of the aperture location. One or the other of the obturator 24 and sleeve 22 presents a sharp tip (not shown) to penetrate breast tissue. For instance, if using a sleeve 22 having an open end, an obturator may provide a sharp tip.

The obturator 24 is inserted into the sleeve 22 and the combination is guided by the track 98 to a proper orientation until an accurate depth is reached as set by the depth stop 26. Once fully inserted, the depth stop 26 prevents over-insertion. The sleeve 22 advantageously latches to the track 98 and/or the depth stop 26 to prevent inadvertent retraction, such as when the obturator 24 is withdrawn, and pressure is received from the breast tissue or later when a probe 100 of the MRI biopsy device 14 is withdrawn from the sleeve 22.

The gantry is moved into the MRI machine bore and the patient is imaged again to confirm placement of the sleeve 22 with respect to the suspicious lesion. Advantageously, imagable materials of the sleeve 22 and/or obturator 24, perhaps comprising or including marker material, enhance the ability to confirm the location of the sleeve 22 and its sleeve side aperture 102 as positioned for subsequent biopsy samples.

Figure 2:
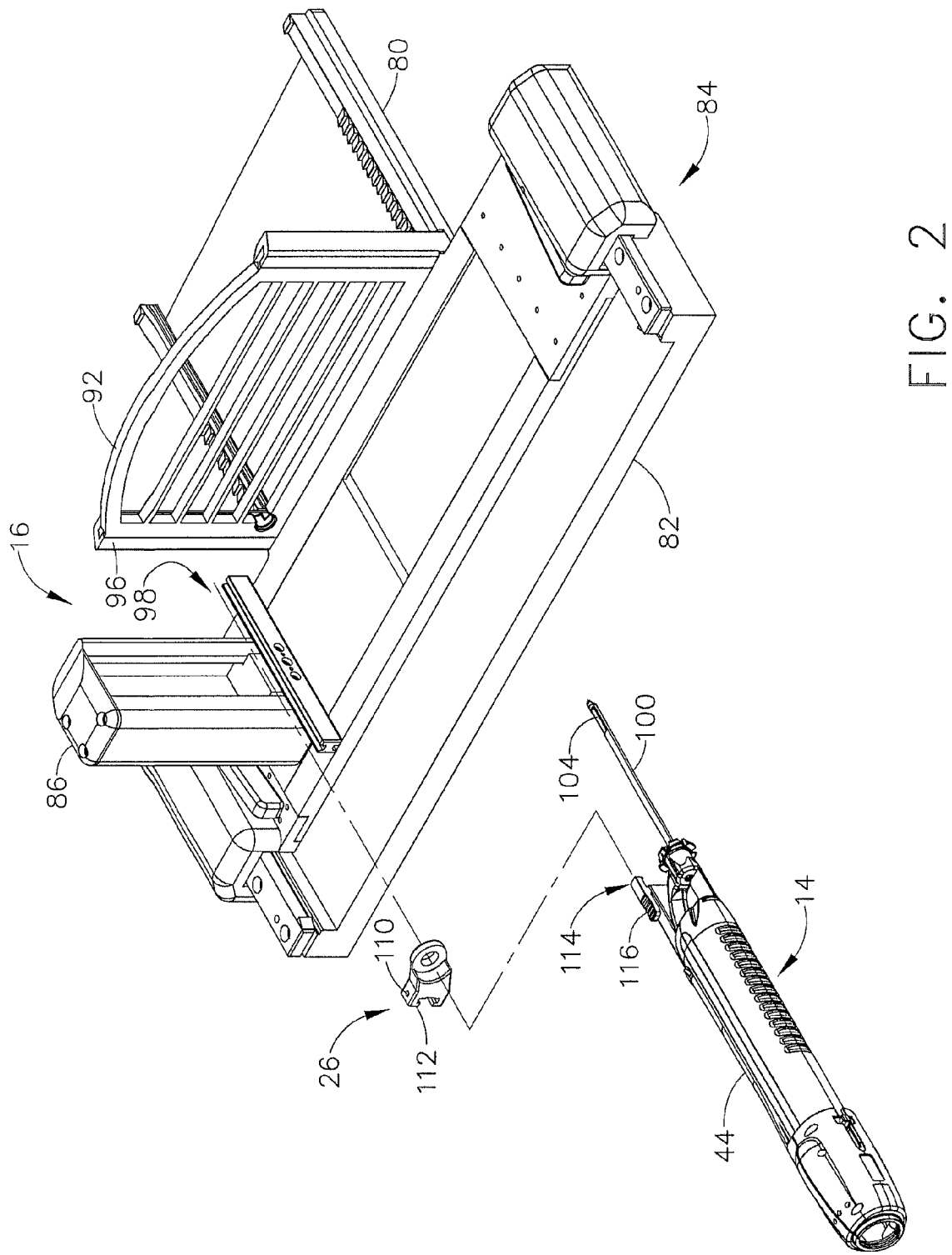
FIG. 2 is a disassembled perspective view of a localization fixture, and a depth stop and MRI biopsy device of the elemental version of the MRI biopsy system of FIG. 1.
Figure 3:
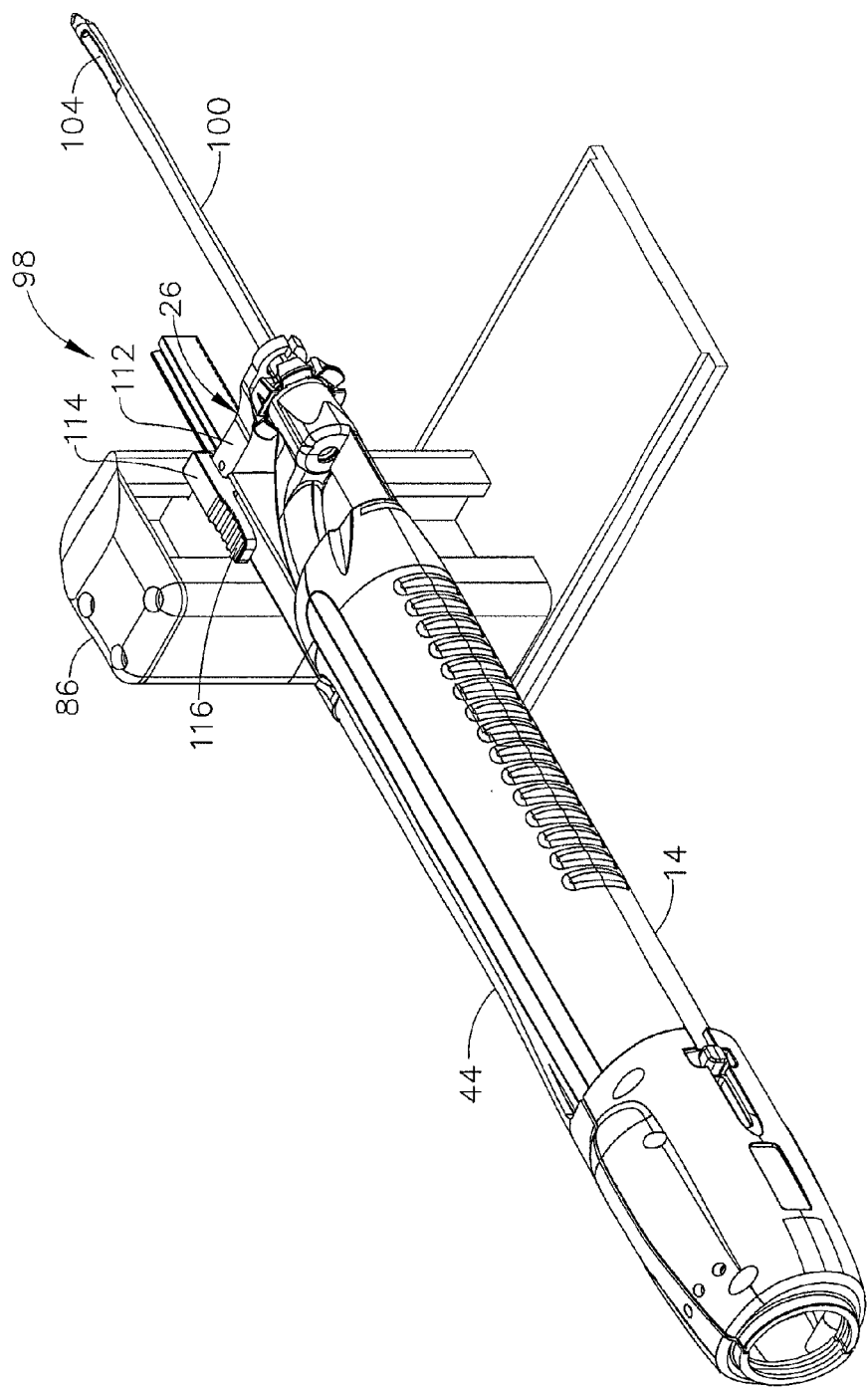
FIG. 3 is a perspective view of a positioning pedestal and a single targeting rail of the elemental version of the MRI biopsy system of FIG. 1 after positioning of the depth stop and MRI biopsy device.

The patient is removed from the MRI machine by retracting the gantry and the holstered MRI biopsy device 14 is brought to the localization fixture 16. A protective cap (not shown) is removed from the probe 100 of the MRI biopsy device 14 and the obturator 24 is removed from the sleeve 22. Mounting of the holster 44 to the track 98 is shown in FIGS. 2 and 3, wherein the holster 44 and MRI biopsy device 14 combination slide onto the track 98 that has been positioned at a certain location with respect to the pedestal 86 and lateral assembly 84. Features of the sleeve 22 and probe 100 may advantageously visually and mechanically orient a probe side aperture 104 of the probe 100 with the sleeve side aperture 102, as well as forming a gas seal. Advantageously, the holster 44 and/or the probe 100 may latch onto the track 98 or sleeve 22 to confirm full insertion and prevent over-insertion and inadvertent retraction. The holster 44 allows an MRI biopsy device 14 intended for handheld use to have sufficient support in its attachment to the localization fixture 16 to accurately maintain its position and to avoid or minimize loads carried by the probe 100.

Thereafter, the MRI biopsy system 10 may take tissue samples by activating a cutter mechanism in conjunction with vacuum assist, withdrawing the cutter and withdrawing a tissue sample, the latter perhaps also with vacuum assist. The probe 100/sleeve 22 combination are capable of manual, or perhaps automatic, rotation to a desired angle with respect to their longitudinal axis for additional samples or additional samples may be taken at the current orientation by further resorting to vacuum assist. The cutter is then advanced to close the probe side aperture 104 and the holster 44 is withdrawn from the localization fixture 16, thereby removing the probe 100 from the sleeve 22.

Additional steps or combinations of steps may be performed at this point such using the probe 100, a specialized obturator 24 (e.g., stylet), or merely the sleeve 22 to guide various agents to the surgical site of the biopsy. Examples include draining fluids, inserting anesthetic agents, inserting hemostatic agents, insufflating with pneumatic pressure and inserting a marker for subsequently locating the site of the biopsy, or other diagnostic or therapeutic procedures.

The patient is then typically drawn back into the MRI machine bore for reimaging to confirm removal of at least a portion of the suspicious lesion and possibly placement of a marker. During this reimaging, the sleeve 22 is sealed with the obturator or stylet 24. Thereafter, the localization fixture 16 is removed, the patient bandaged and removed from the gantry, and the disposable portions of the MRI biopsy system 10 disposed of as medical waste.

Elemental Version of Guidance Assembly Incorporating Single Targeting Rail for Depth Stop and Biopsy Device.

With particular reference to FIGS. 2-3, the single targeting rail 98 facilitates sequential mounting of separate components. First the depth stop 26, then the sleeve 22 (as in FIG. 1), and then the biopsy tool 14 is slid onto the single targeting rail 98. Alternatively as depicted in FIGS. 2-3, the single targeting rail 98 may receive the depth stop 26 and then an MRI biopsy device 14 is used without a separate sleeve 22. The maximum depth of penetration into the patient's breast is preset by the location of the depth stop 26 on the single targeting rail 98. An engagement mechanism between the holster 44 and the single targeting rail 98 (not shown) and/or an engagement mechanism formed by a catch, depicted as an upwardly projecting pin 110, on an upper rail-gripping arm 112 of the depth stop 26 and a downwardly spring-biased rocker latch 114 that snaps onto the upwardly projecting pin 110, preventing inadvertent retraction of the MRI biopsy device 14. The holster 44 may be disengaged by downward pressure on a proximal actuating arm 116 of the rocker latch 114.

The single targeting rail 98 may be longitudinally sized to be proximally extending sufficient that the MRI biopsy device 14 engages the single targeting rail 98 prior to the probe 100 contacting the patient's skin. The single targeting rail 98 is also sized to not extend proximally so far as to preclude use in a closed bore MRI machine (not shown). Such a MRI biopsy system 10 is believed to minimize the procedure turn-around time to less than 45 minutes as described above. Yet with this expeditious turn-around, a radiologist may position the probe 100 accurately to within 2 mm (5 mm maximum) of the lesion center. Further, the radiologist may maximize access to both breasts (left or right) during a procedure (both sides of the table) with minimal repositioning of the patient. Further, a minimal amount of force to penetrate tissue is required, such as less than 4 lbs. Although the depth stop 26 serves to prevent overshooting, features for repositioning the depth stop 26 prior to further insertion of the probe 100 allow clinical flexibility in targeting another location.

Orthogonal Targeting and Biopsy Rails ("Cradle").

Figure 4:
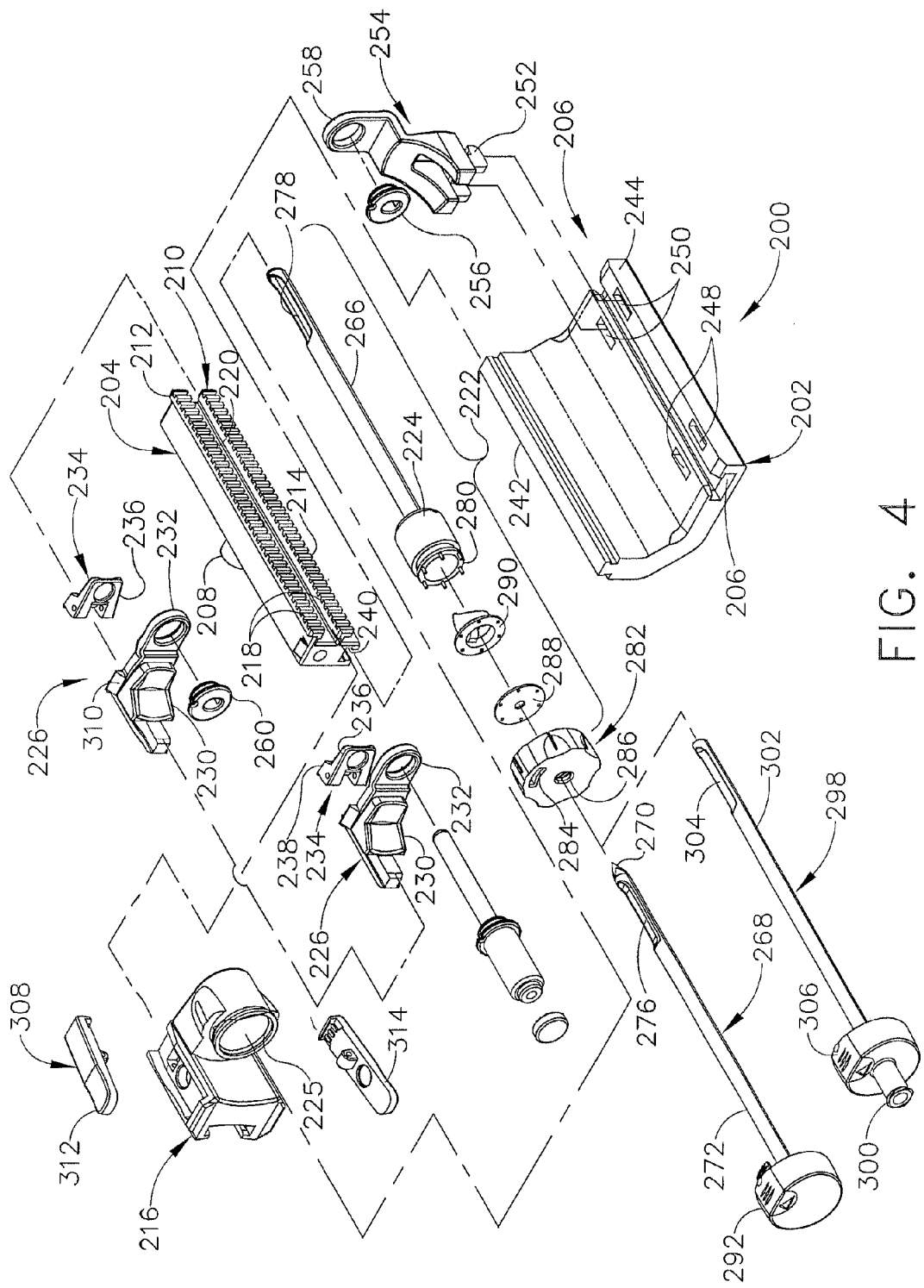
FIG. 4 is a perspective disassembled view of an alternative guidance assembly for the MRI biopsy system of FIG. 1, incorporating orthogonally targeting and biopsy support rails ("cradle")

In FIG. 4, an alternative guidance assembly 200 for the MRI biopsy system 10 incorporates a cradle 202 that attaches to a targeting rail 204 and provides a biopsy rail 206 for supporting the MRI biopsy device, both rails 204, 206 aligned to the Z axis. The targeting rail 204 is attached to the positioning pillar 86 (not shown in FIG. 4) and vertically adjusted to a desired Y-position. A circular attachment point 208 may form a rotational engagement to the positional pedestal 86 to allow an angled targeting guide.

A lateral face 210 of the targeting rail 204 includes an upper flange 212 and a lower flange 214 each having an L-shaped cross section for slidingly receiving a sleeve mount 216. Vertical rows of laterally projecting ridges 218 in each flange 212, 214 serve as a locking surface for the sleeve mount 216. Between the flanges 212, 214, a side channel 220 is recessed therein. The sleeve mount 216 guides a sleeve 222 by having its sleeve hub 224 proximally received in a hub receptacle 225 of the sleeve mount 216 and distally positioned and constrained by a depth stop 226.

The depth stop 226 includes a slide member 228 that engages the side channel 220. A depth stop housing 230 attaches thereto, terminating in a reticule 232. A locking lever 234 is vertically pinned within a distally open recess (not shown) defined in the depth stop 226 with a lateral portion 236 spring biased away therefrom such that distally projecting feet 238 pivot against and engage the ridges 218, especially against a proximal movement. Depressing the lateral portion 236 proximally against the distally open recess of the depth stop housing 230 releases the distally projecting feet 238 to allow repositioning the depth stop 226 distally.

An axis of penetration of the biopsy device 10 is aligned with the axes defined by the targeting rail 204 and the biopsy rail 206, which are laterally and vertically orthogonally offset therefrom, respectively. Extending a horizontal plane from the targeting rail 204 and extending a vertical plane from the biopsy rail 206 intersect at a common centerline that is the axis of penetration. Having the biopsy rail 206 vertically aligned and parallel to the axis of penetration advantageously provides support for the weight of the biopsy device 14 with a minimum of torsion loads that may otherwise create deflections of an inserted distal end. Thereby, even for a relatively heavy and elongated device, positioning and maintaining its distal end is achievable within 5 mm, and even 2 mm, of a desired insertion point. Thereby, a "hands free" procedure may be performed, avoiding the inconvenience or the impracticabilitxis of penetration in the illustrative version may be replaced by one vertically displaced above the axis of penetration. In particular, having a cradle that may be engaged to either side of the targeting rail 204 would provide further vertical symmetry to take full advantage of the space afforded by the breast coil 18.

While a "hands free" capability is advantageous for a single insertion/multiple sample biopsy device, it should be appreciated that such penetration guidance with a preset depth stop as described herein has application to even lightweight biopsy devices that employ a core needle biopsy with a single insertion per single sample. In particular, correct placement need not be conditional on continuous imaging. Over penetration during insertion and inadvertent displacement is avoided when hands are free.

A bottom dovetail channel 240 in the targeting rail 204 receives a top dovetail extension 242 on the cradle 202, which is slid therein. It should be appreciated that mounting is shown herein on the right side of the positioning pedestal 86 when viewed proximally, but that the guidance assembly 200 advantageously comprises symmetric parts that allow mounting and use on either side of the positioning pedestal 86 to increase flexibility in positioning the probe 100. Thus, a horizontal base 244 of the cradle 202 forms the biopsy rail 206 as a biopsy guide channel 246 flanked by a first and second pair of monocle receptacles 248, 250 so that a pair of locking hooks 252 on a monocle 254 may be inserted in either pair of monocle receptacles 248, 250, depending on which is closer to the patient. Rather than mounting the cradle 202 to the targeting rail 204 as depicted, the cradle may be directly attached to the positioning pedestal 86 (not shown). The cradle 202 is mechanically robust and can support the gross weight of the MRI biopsy device 14. Since the MRI biopsy device 14 does not share the cradle 202, the cradle 202 may be optimized to support the MRI biopsy device 14 when either shallow or deep lesions need to be accessed.

A guide bushing 256 inserted in a monocle reticule 258 guides a marking instrument and/or a scoring scalpel (not shown) as an initial step in locating and preparing an insertion point. The monocle 254 may be removed thereafter or left in place to guide the sleeve 222 in addition to the reticule 232 of the depth stop 226, the latter which may also hold a guide bushing 260 for guiding the sleeve 222. Removing the guide bushings 256, 260 allows for the reticules 258, 232 of the monocle 254 and depth stop 226 to guide a larger component, such as a fiducial 262 used for locating a suspicious lesion relative to the guidance assembly 200.

The alignment of the sleeve 222 is maintained by first passing through the hub receptacle 225 of the sleeve mount 216, which receives the sleeve hub 224. In the illustrative version, the sleeve 222 has an open ended shaft 266 for receiving an obturator 268 that includes a piercing tip (e.g., flat blade) 270 at a distal end of solid obturator shaft 272. A beveled recess 276 into the solid obturator shaft 272 is aligned with a sleeve side aperture 278 of the sleeve 222, and thus ultimately of the probe 100 (FIGS. 1-3). The materials of the obturator 268 may be selected to aid in locating the sleeve side aperture 276 of the sleeve 222, which otherwise may be more difficult to visualize and locate in an MRI scan slice.

The sleeve hub 224 has its proximal cylindrical edge 280 attached to a guidance thumbwheel 282 that proximally extends from the hub receptacle 225 of the sleeve mount 216 for rotating the sleeve 222 to position its sleeve side aperture 278 with reference to a visual mark, depicted as a locking slot 284, on the thumbwheel 282 corresponding thereto. The thumbwheel 282 includes a central through hole 286 sealed by a wiper seal 288 and a duckbill seal 290 trapped between the thumbwheel 282 and the proximal cylindrical edge 280 of the sleeve hub 224. Thus insertion of the obturator 268, which includes a locking tab 292 that enters the locking slot 284, closes the central through hole 286 and forms a dynamic seal against the wiper seal 288.

After removing the obturator 268, a stylet 298 may be inserted into the sleeve 222 so that a proximally presented hose nib 300 of the stylet 298 may be used to insufflate the surgical site or used for other purposes such as draining bodily fluids or inserting therapeutic or diagnostic agents through a stylet shaft 302 of the stylet 298 to a stylet side aperture 304 that is aligned with the side aperture 278 of the sleeve 222. The stylet 298 also includes a locking tab 306.

The sleeve mount 216 includes a downwardly spring-biased rocker latch 308 that snaps onto a ramped catch 310 on the depth stop 226, preventing inadvertent retraction of the sleeve 222. The sleeve mount 216 may be disengaged by downward pressure on a proximal actuating arm 312 of the rocker latch 308. An upwardly spring-based rocker latch 314 attached to the bottom of the sleeve mount 216 similarly engages the depth stop 226. Thus, after the depth stop 226 is set on the targeting rail 204 to a desired depth of insertion, the sleeve mount 216 may be distally advanced without overshooting and subsequently be held in place when removing implements therefrom such as the obturator 268, stylet 298, and MRI biopsy device 14.

Second Rail Elemental Integration of Z-Stop Feature into Sleeve Mount.

Figure 5:
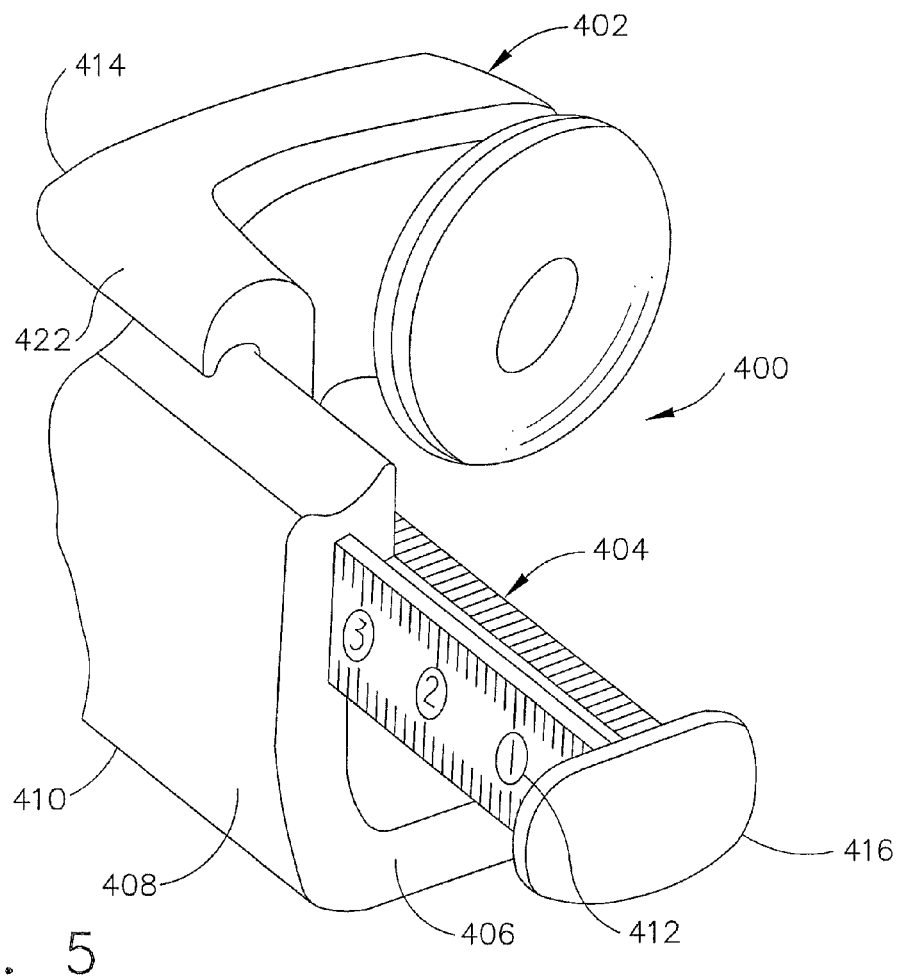
FIG. 5 is a perspective view of a cradle engaging a depth stop second rail, depicted as locked, of another alternative guidance assembly for the MRI biopsy system of FIG. 1.
Figure 5A:
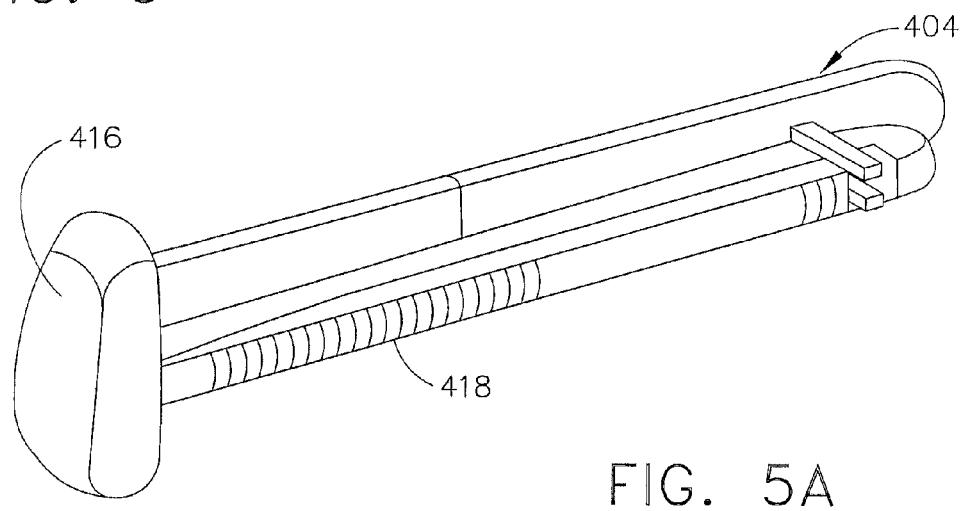
FIG. 5A is a perspective view of the depth stop second rail of FIG. 5, depicted as locked.
Figure 5C:
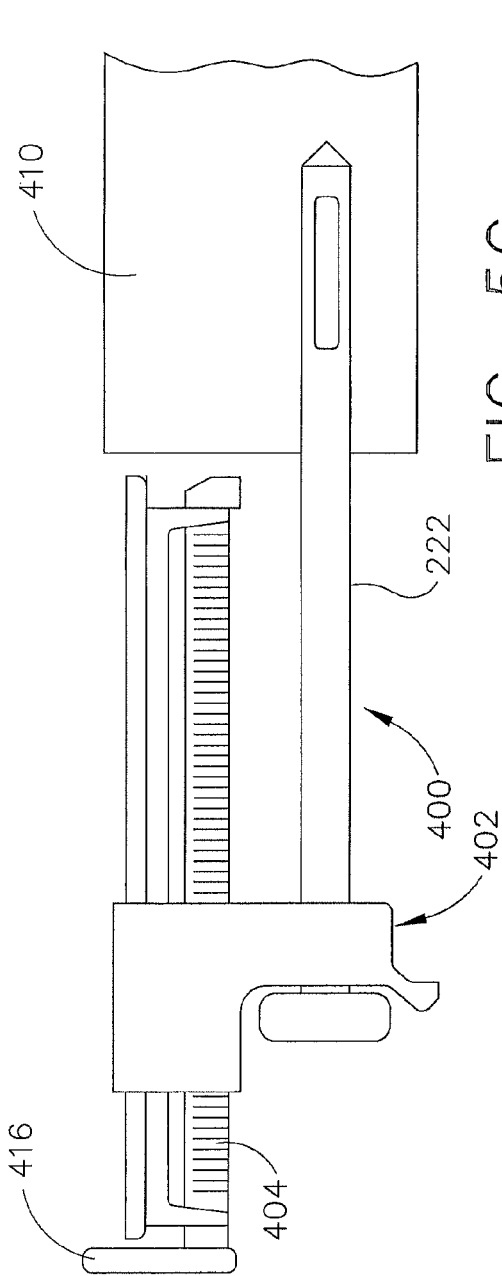
FIG. 5C is a top view of the depth stop second rail of FIG. 5 aligned for insertion into the cradle for insertion of a sleeve.
Figure 5D:
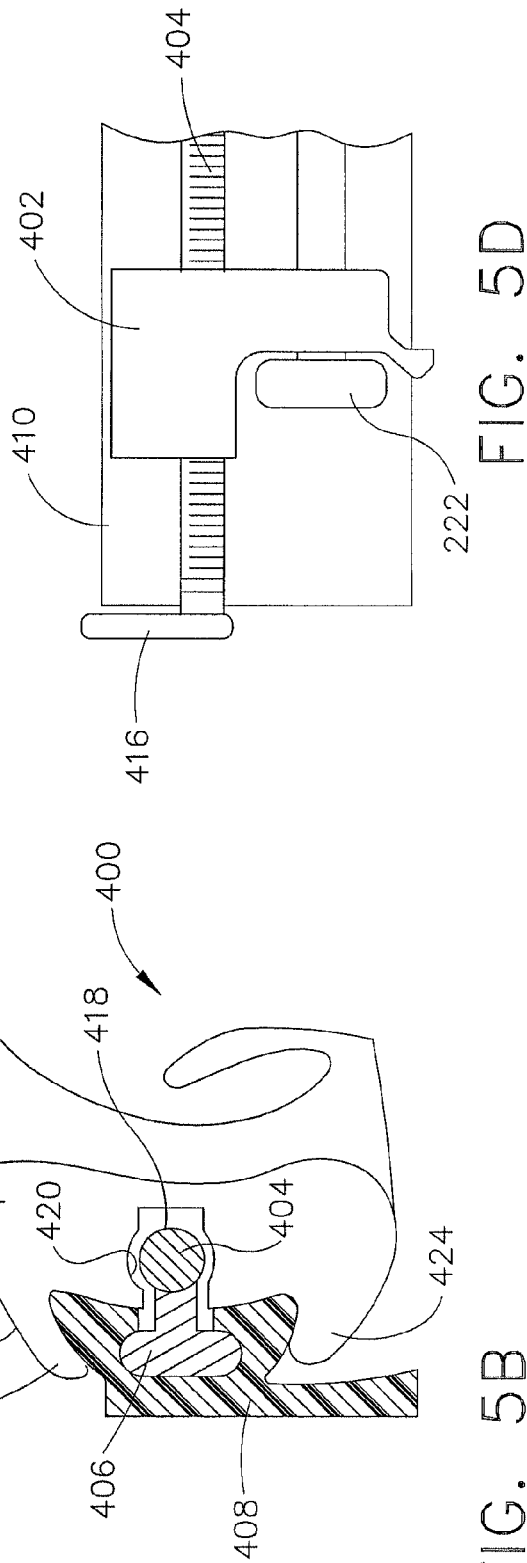
FIG. 5D is a top view of the depth stop second rail of FIG. 5C after insertion into the cradle.
Figure 5B:
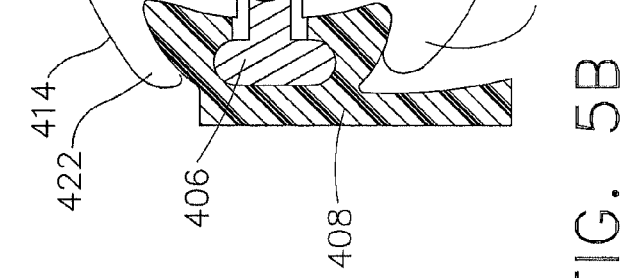
FIG. 5B is a proximal view in elevation of the cradle and depth stop second rail taken in cross section along lines 5B-5B of FIG. 5.

In FIG. 5, another alternative depth guidance assembly 400 for the MRI biopsy system 10 of FIG. 1 advantageously integrates a sleeve mount 402 with a depth stop second rail 404. A depth stop guide tab 406 of the guidance assembly 400 is sized to slide into a tracking lateral channel 408 of a cradle 410. Depth measurement indicia 412 (FIG. 5) on the guide tab 406 assist in prepositioning a sleeve block 414 prior to insertion. In FIG. 5A, a locking actuator 416 on a proximal end of the depth stop second rail 404 is rotated 90 degrees clockwise as viewed proximally to disengage a threaded or ridged side 418 of the depth stop second rail 404 laterally out of threaded engagement with an inner recess 420 of the sleeve block 414 (FIG. 5B) thereby allowing gross adjustment. Then the sleeve block 414 is locked onto the depth stop second rail 404 by rotating the locking actuator 416 counterclockwise (FIGS. 5, 5B, 5C) and then inserting the guide tab 406 into the tracking lateral channel 408 of the cradle 410 until further insertion is blocked by locking actuator 416 abutting the cradle 410 (FIG. 5D). The sleeve block 414 includes upper and lower gripping flanges 422, 424 that lock onto upper and lower guides 426, 428 (FIG. 5B) that define the tracking lateral channel 408, providing a robust support for the sleeve 222 (FIGS. 5C, 5D).

Figure 6:
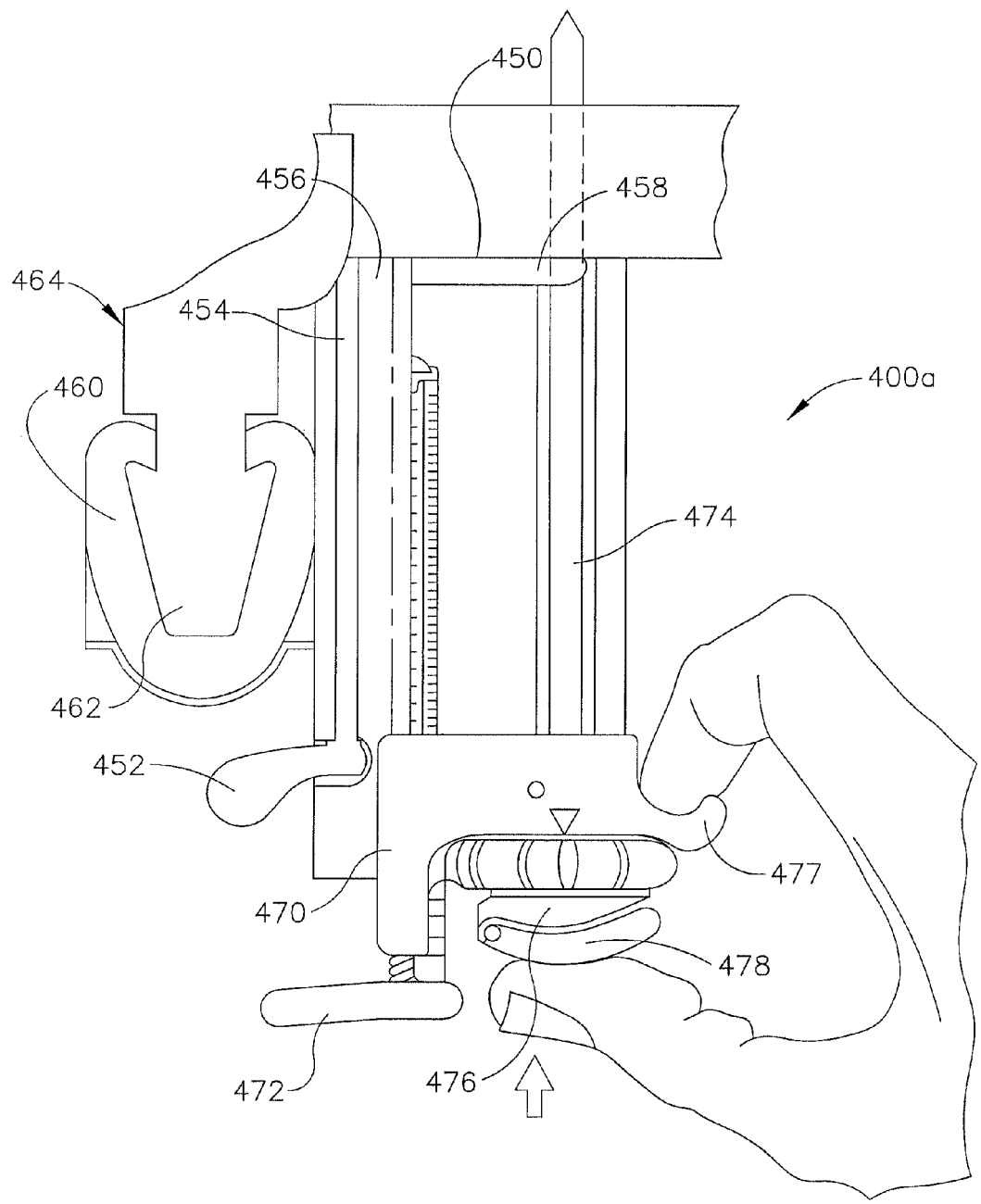
FIG. 6 is a top view of an alternative depth guidance assembly with a flip monocle and a side lever that unlocks a sleeve block 470 for the MRI biopsy system of FIG. 1.

In FIG. 6, a depth guidance assembly 400a further includes a flip monocle 450 with a proximal flag 452 that allows rotating a monocle shaft 454, which snaps into a top surface of a cradle or carriage 456, to ultimately rotate a monocle reticule 458 either laterally or up and out of the way. The cradle 456 is attached in this version to a gripping clasp 460 that vertically slides up a proximal vertical portion 462 of a pedestal or pillar 464 that has a blunted arrowhead horizontal cross section. A sleeve block 470 advantageously includes a backside lever 472 allowing insertion of a sleeve 474 and obturator 476 by pushing in a manner familiar to surgeons with typical needle biopsies. A forefinger depresses a side lever 477 that unlocks the sleeve block 470 and allows the slide block 470 to be distally pushed forward by a thumb. Releasing the side lever 477 allows the slide block 470 to lock into place. Removal is performed by depressing the backside lever 472 in a similar manner. Since the flat of the thumb is easily able to exert a force of 5 lbs, this is a more comfortable method for the surgeon than using other contact points on the hand. The obturator 476 is released in this version by lifting up a cap lever 478 that rotates 180 degrees from a pivot point 480 at one side of an obturator cap 482 that is easy to grip as compared to small rings as typically used.

Second Rail Sleeve Mount with Elemental Knuckle Mediated Rough Adjust.

Figure 7:
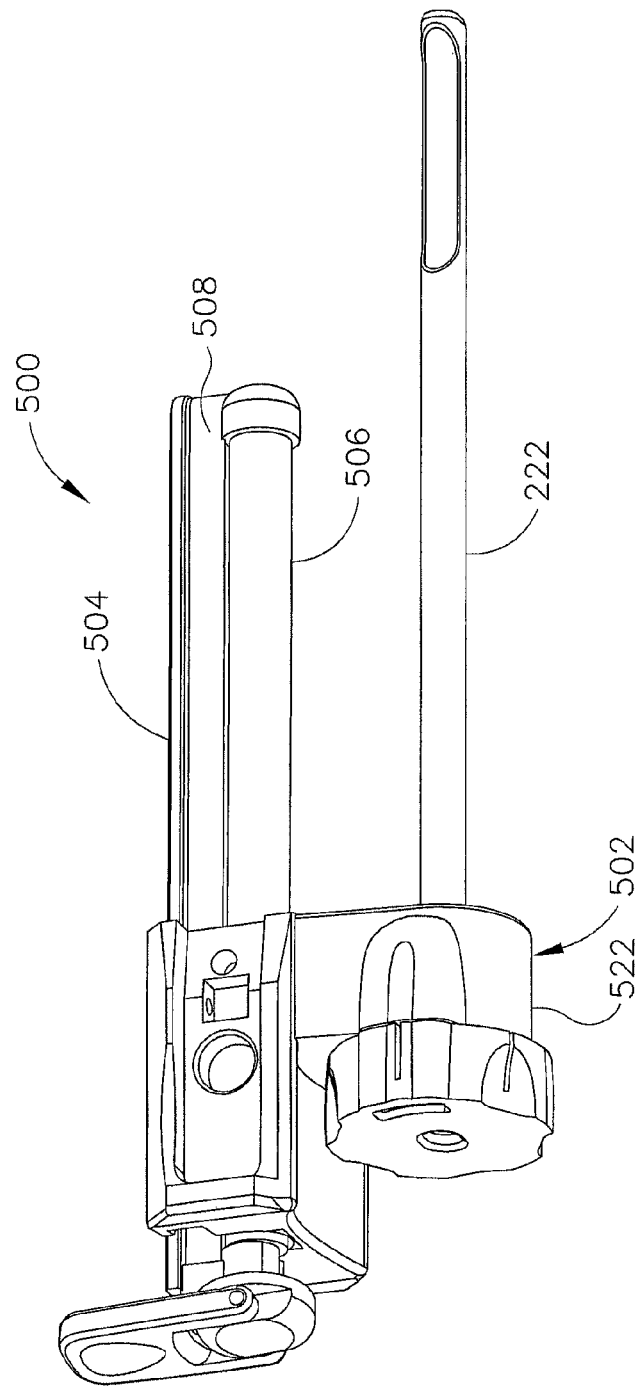
FIG. 7 is a top right perspective view of an additional depth guidance assembly with a knuckle mediated rough adjust for the MRI biopsy system of FIG. 1.
Figure 8:
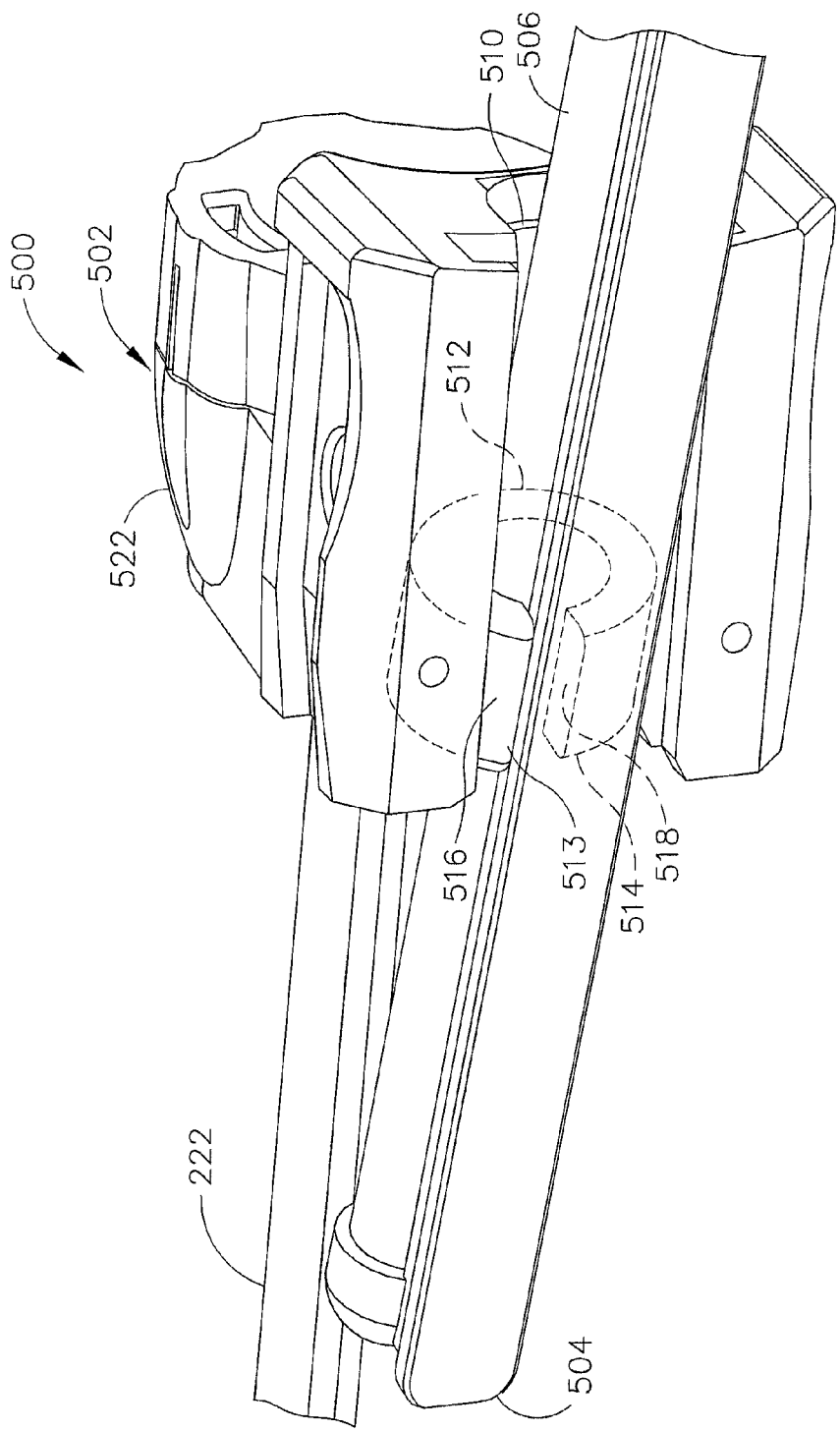
FIG. 8 is a left, proximal perspective view of a mediated knuckle and sleeve block with a guide tab and depth-stop second rail (screw) shown in phantom of the depth guidance assembly of FIG. 7.
Figure 9:
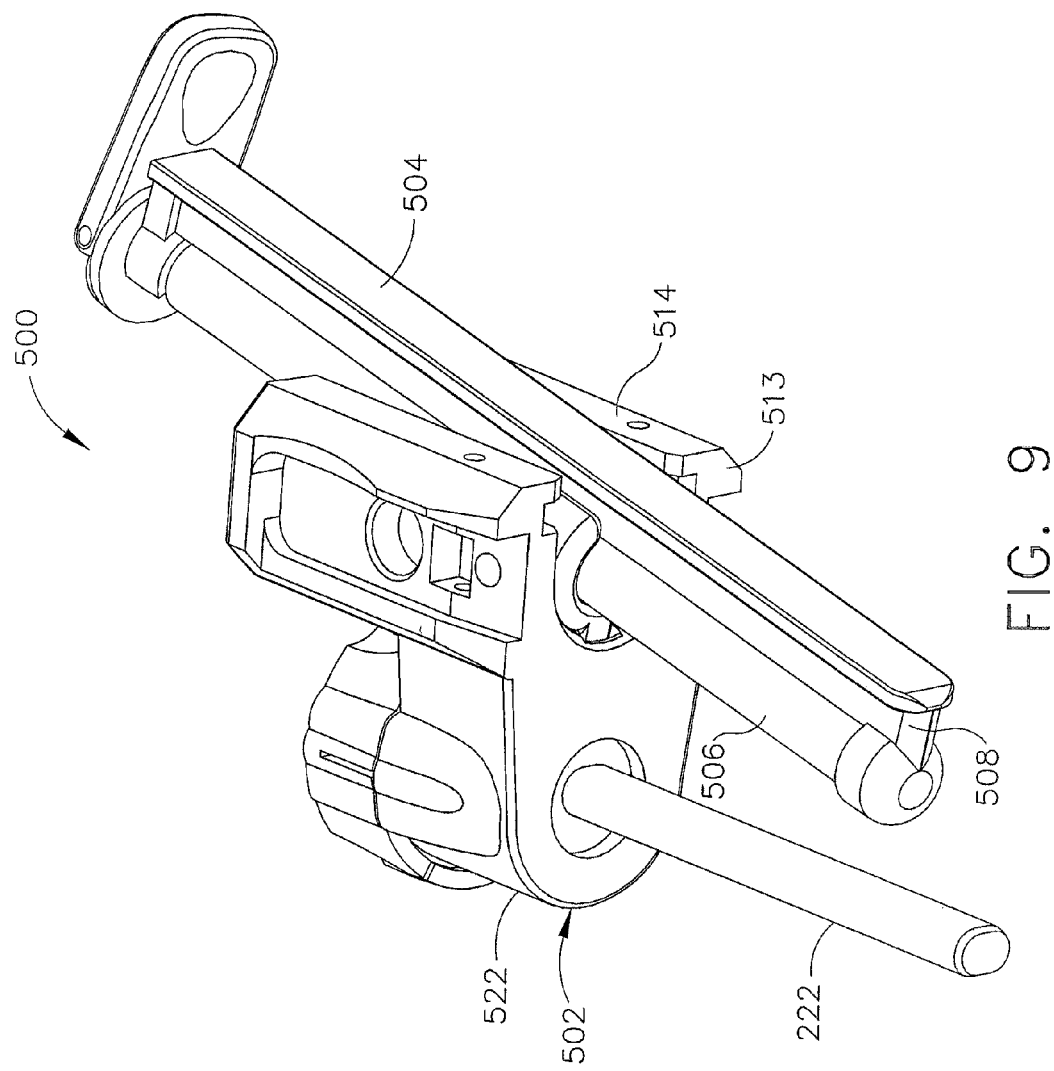
FIG. 9 is a top, left, and distal perspective view of the depth guidance assembly of FIG. 7.
Figure 10:
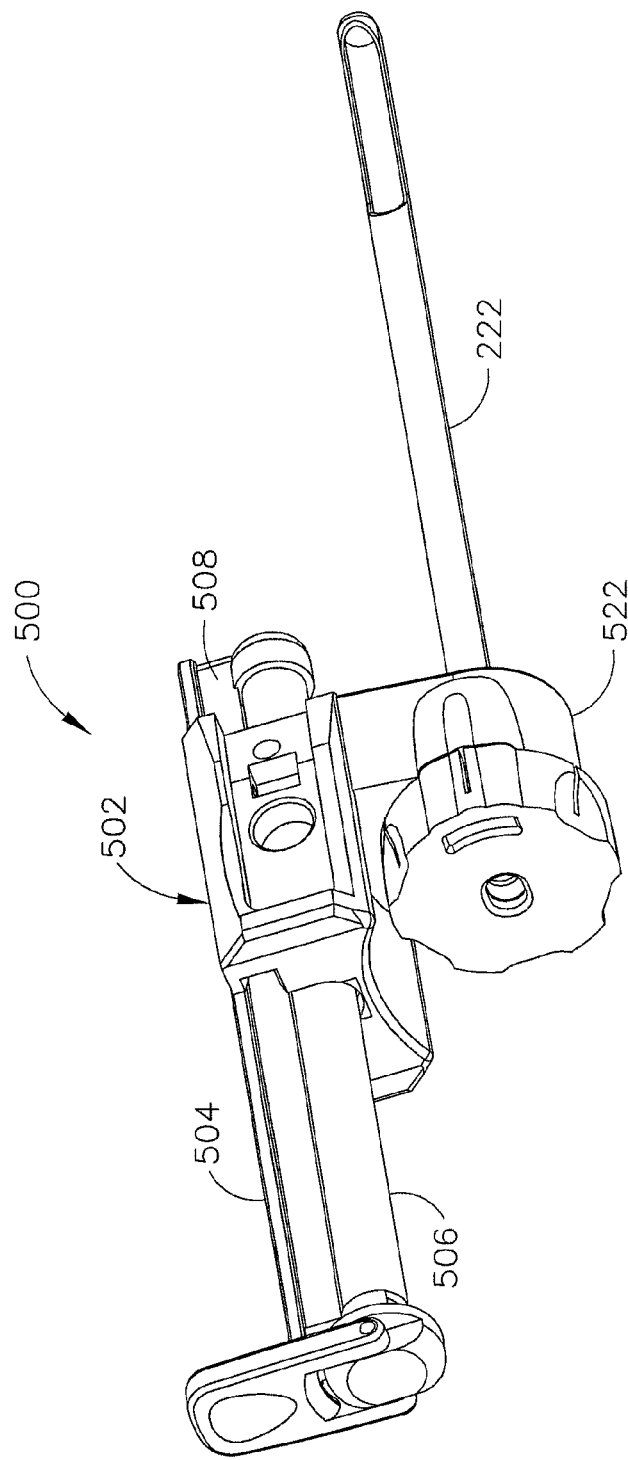
FIG. 10 is a top, proximal, perspective view of the depth guidance assembly of FIG. 7, distally adjusted for additional depth.
Figure 10A:
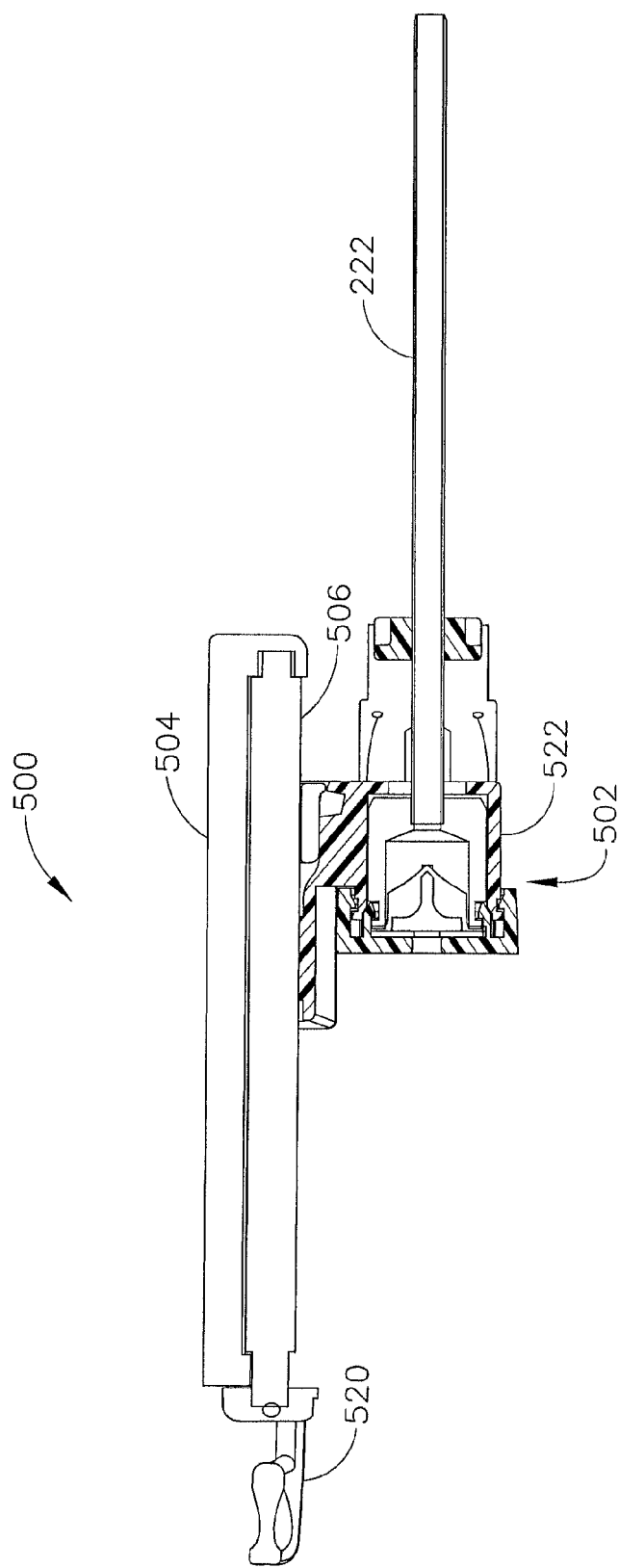
FIG. 10A is a top view of the depth guidance assembly of FIG. 10 in longitudinal cross section.

In FIG. 7, yet another depth guidance assembly 500 with a sleeve block 502 having a guide tab 504 spaced apart from a depth stop second rail 506 by a beam 508 is shown. In FIG. 8, the sleeve block 502 includes a proximal half cylindrical recess 510 that receives an outward portion of the depth stop second rail 506. A distal half cylindrical recess 512, which is aligned with the proximal half cylindrical recess 510, has an increased inner diameter to receive a resilient knuckle 513 that is shaped as a cylindrical bushing with a longitudinal gap 514. Thus, upper and lower ends 516, 518 of the knuckle 513 (FIG. 8) opposingly grip the depth stop second rail 506 and abut the beam 508. Yet, the knuckle 513 allows mediation of the sleeve block 502 as depicted in FIGS. 8-9. When unmediated as in FIG. 7, the sleeve block 502 and depth stop second rail 506 form a worm gear engagement such that rotating a screw handle 520 at a proximal end of the depth stop second rail 506 may be used for fine adjustment of the depth position of the sleeve block 502, and thus a sleeve mount 522 and sleeve 222. In particular, the initial depth is set outside the MRI machine ("coil") (not shown) with the knuckle 513 and the depth stop second rail ("screw") 506 for fine control. If additional depth is desired, the sleeve block 502 is locked to the primary targeting rail (not shown), the screw 506 is backed out the desired additional depth, as depicted in FIGS. 10, 10A, and then the sleeve block 502 is pushed into the new depth with a single motion until the screw handle 520 hits the back of the primary targeting rail.

Second Rail Sleeve Mount with Rough Adjust and Release Buttons.

Figure 11A:
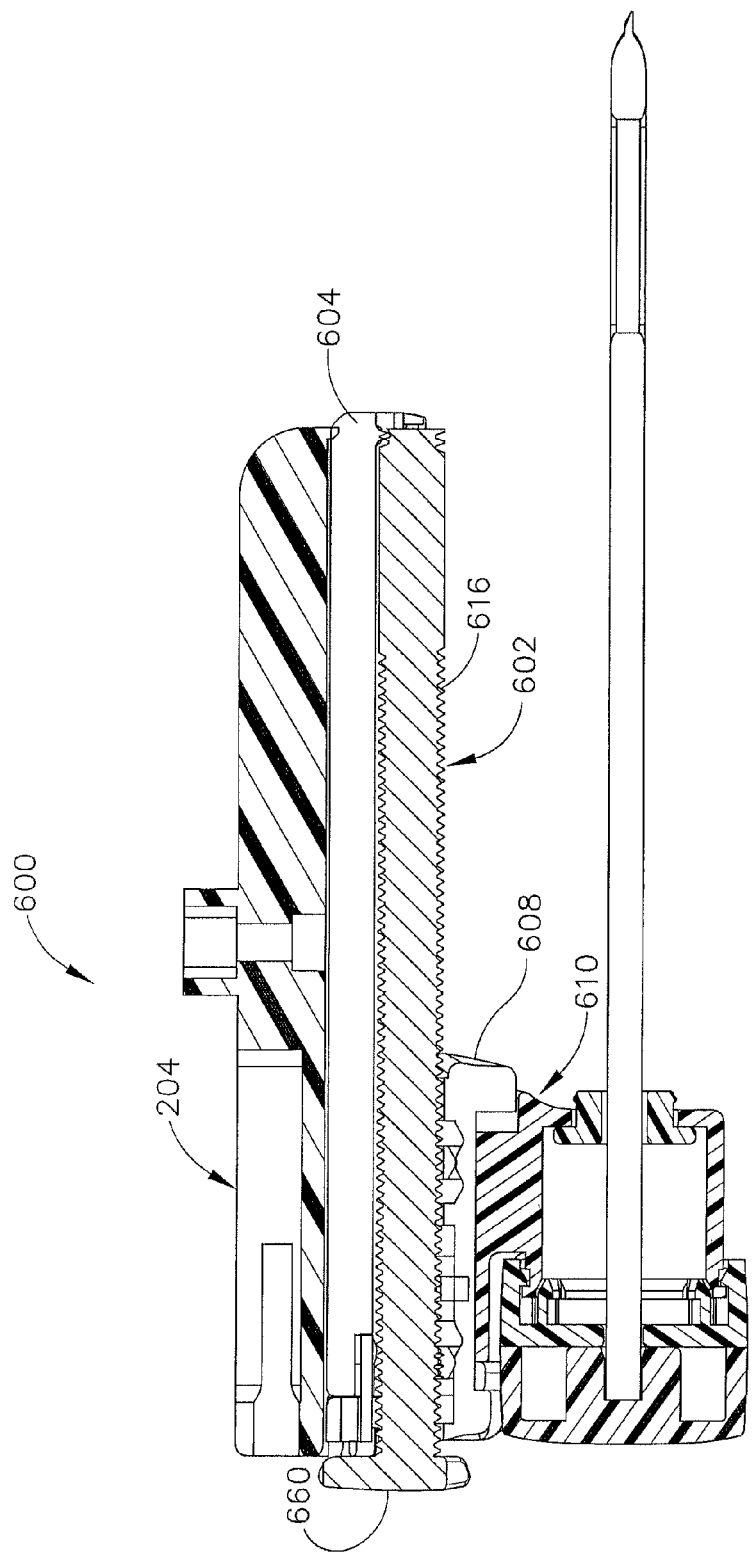
FIG. 11A is a top view in longitudinal cross section of the depth guidance assembly with rough adjust and release buttons of FIG. 11 fully inserted into a targeting single rail.
Figure 11B:
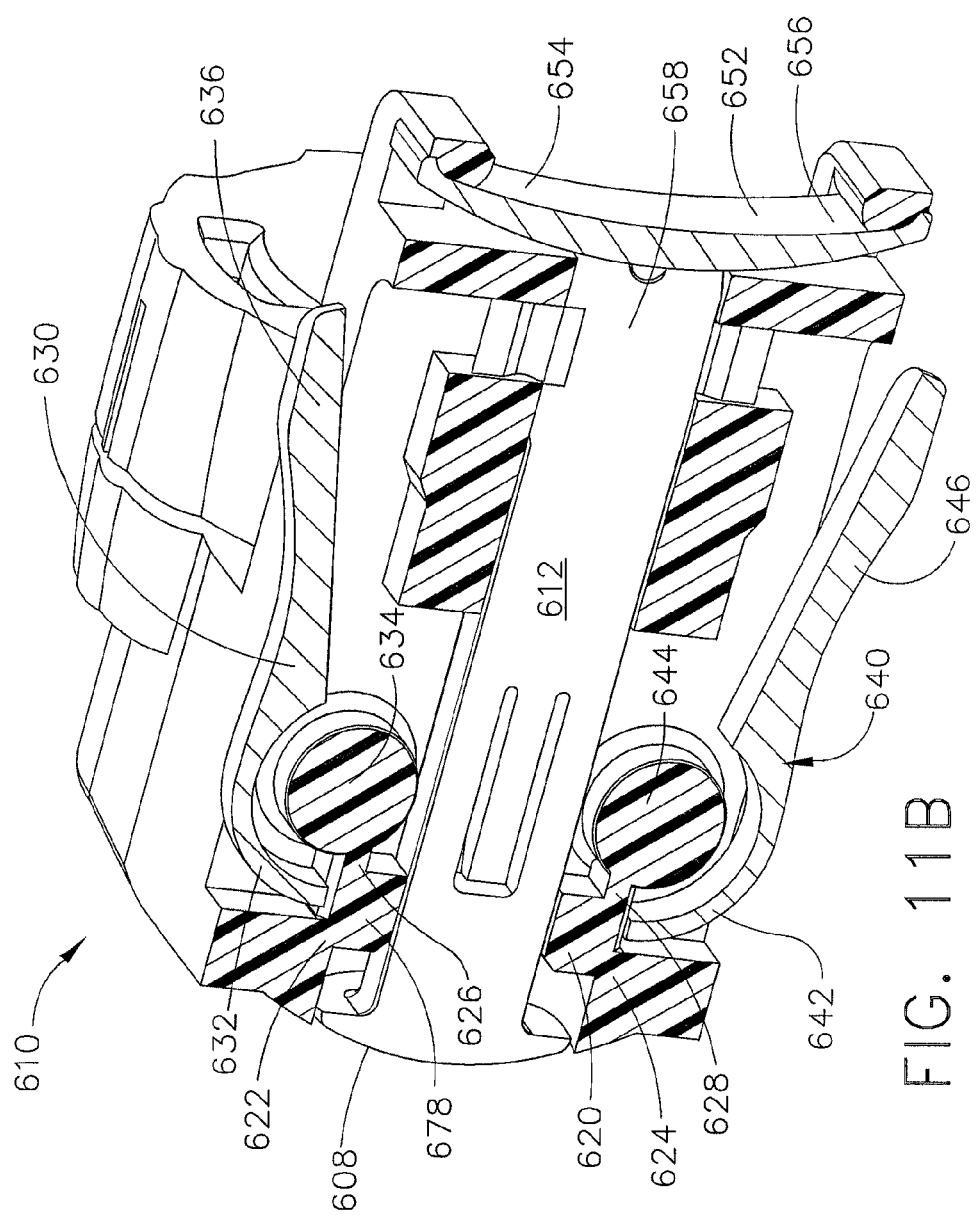
FIG. 11B is a left, proximal and perspective view of a sleeve block cutaway along lines 11A-11A of the depth guidance assembly of FIG. 11.

In FIGS. 11, 11A, 11B, 12, 13 and 13A, yet an additional depth guidance assembly 600 includes a depth stop second rail (screw) 602 held parallel to a guide tab 604 that slides into the primary targeting rail 204 (FIGS. 11, 11A, 12, 13, 13A)

that is set at a desired Y-axis position. A rough adjust button 608 is presented toward the back (distal) side of a sleeve block 610 so as to discourage its use after insertion into the primary targeting rail 204 (FIG. 11). Depressing the rough adjust button 608 proximally translates a locking plate 612 (FIG. 11B) having a distally projecting and inwardly biased spring finger 614, drawing the latter out of engagement with outer threads 616 on the depth stop second rail 602 allowing rough adjustment.

With particular reference to FIG. 11B, the locking plate 612 is pinched between rectangular upper and lower structures 618, 620, which are attached at their more vertically displaced distal corners 622, 624 and proximal corners 626, 628 respectively. A top release lever arm 630 has a downwardly arcing distal portion 632 that is attached to the rectangular upper structure 618 between distal and proximal corners 622, 626, and is biased upwardly and spaced away from an upper lateral cylindrical structure 634 attached to the proximal corner 626. A proximally and upwardly extending handle portion 636 of the top release lever arm 630, when pushed inwardly (down), causes the arcing distal portion 632 to contact the upper lateral cylindrical structure 634, prying the rectangular upper structure 618 away from the locking plate 612. Similarly, a bottom release lever arm 640 has an upwardly arcing distal portion 642 that is attached to the rectangular lower structure 620 between distal and proximal corners 624, 628, is biased downwardly and spaced away from a lower lateral cylindrical structure 644 attached to the proximal corner 628. A proximally and downwardly extending handle portion 646 of the bottom release lever arm 640, when pushed inwardly (up), causes the arcing distal portion 642 to contact the lower lateral cylindrical structure 644, prying the rectangular lower structure 620 away from the locking plate 612. With both top and bottom release lever arms 630, 640 depressed by release buttons 650 (top one shown in FIGS. 11, 11B, 12, 13 and bottom one not shown), a vertical leaf spring 652 (FIG. 11B), held at its upper and lower ends 654, 656 in the sleeve block 610, is allowed to bias a proximal end 658 of the locking plate 612 and thus the rough adjust button 608 distally. Thereby, the sleeve block 610 is locked again to the depth stop second rail 602.

Figure 12:
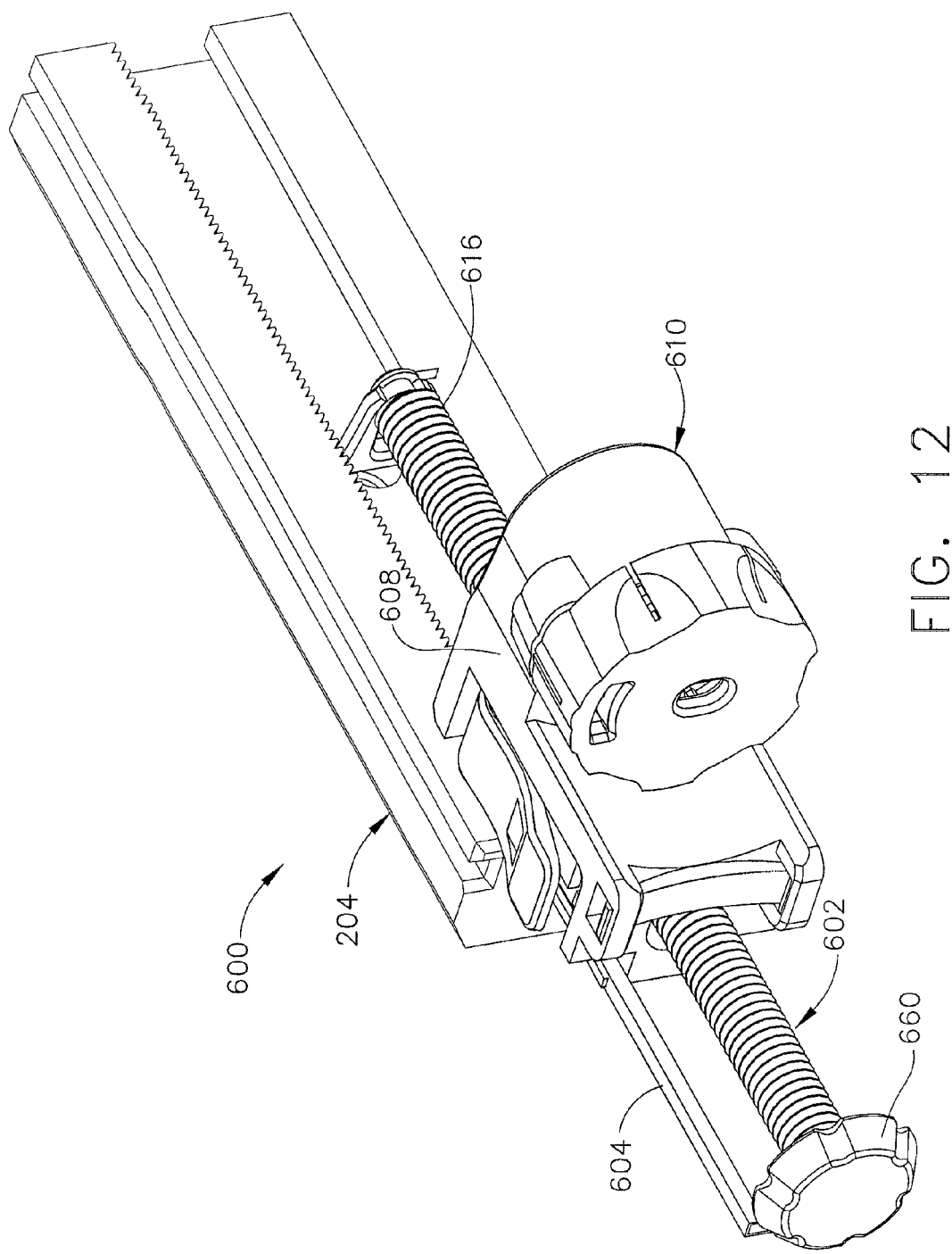
FIG. 12 is a top, proximal and right perspective view of the depth guidance assembly of FIG. 11 after being partially inserted into the primary targeting rail.
Figure 13:
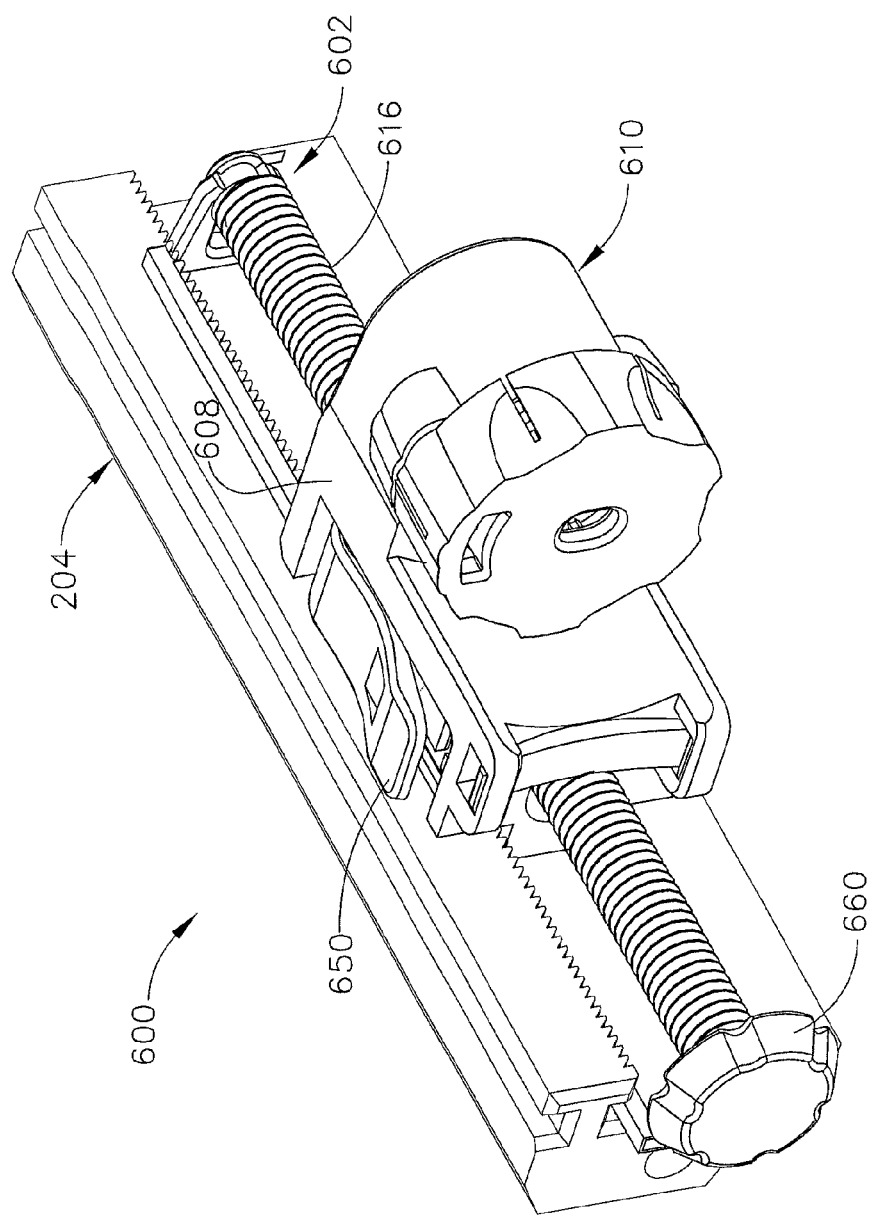
FIG. 13 is a top, proximal and right perspective view of the depth guidance assembly of FIG. 11 after being fully inserted into the primary targeting rail.

In use, the rough adjust button 608 is depressed to allow positioning the sleeve block 610 when detached from the primary targeting rail 204 (FIG. 11). When close to the desired position, the release buttons 650 are depressed to lock the screve block 610 to the depth stop second rail (screw) 602 and to deactivate the rough adjust button 608. Then a screw handle 660 is turned at the proximal end of the depth stop second rail 602 is refine the position. Additionally, the depth guidance assembly 600 is attached by sliding the guide tab 604 into the primary targeting rail 204 (FIGS. 12, 13). If additional depth is desired, the sleeve block 610 is locked to the primary targeting rail 204, the screw 602 is backed out the desired additional depth, and then the sleeve block 610 is pushed into the new depth with a single motion until the screw handle 660 hits the back of the primary targeting rail 204.

Telescoping Depth Guidance Assembly.

Figure 14:
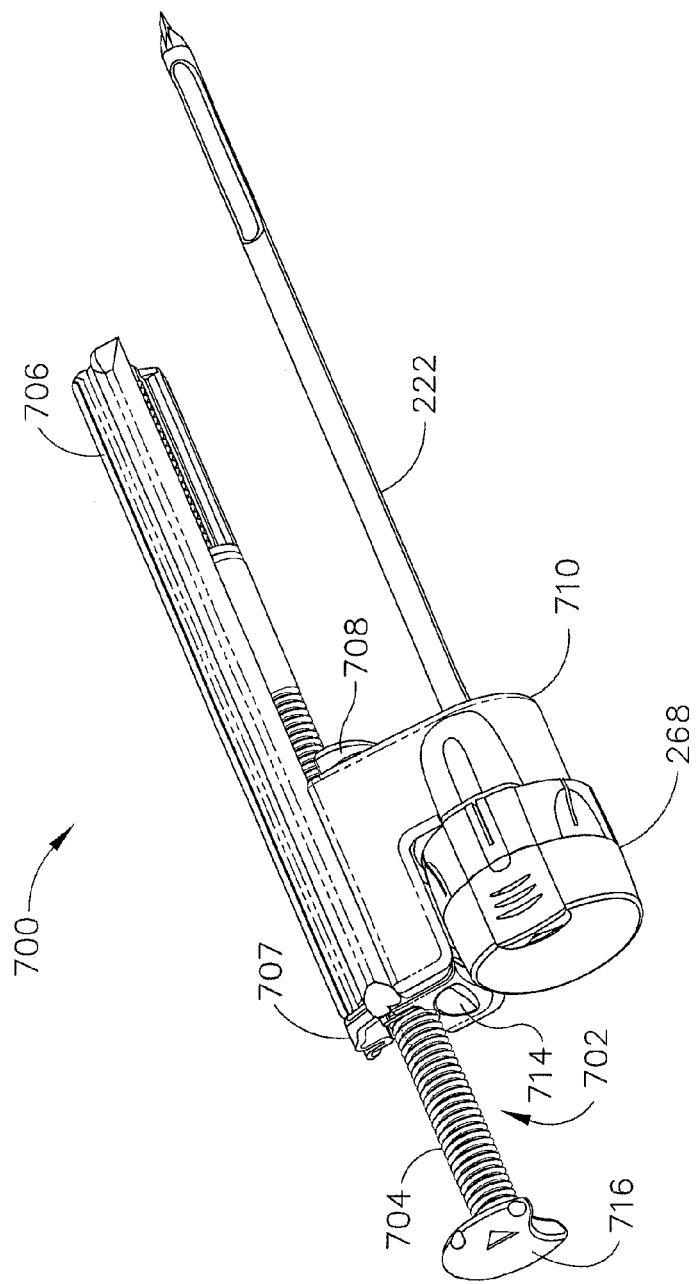
FIG. 14 is a top, proximal and right perspective view of a telescoping depth guidance assembly with a sleeve and obturator for the MRI biopsy system of FIG. 1 engaged to a sleeve block.
Figure 14A:
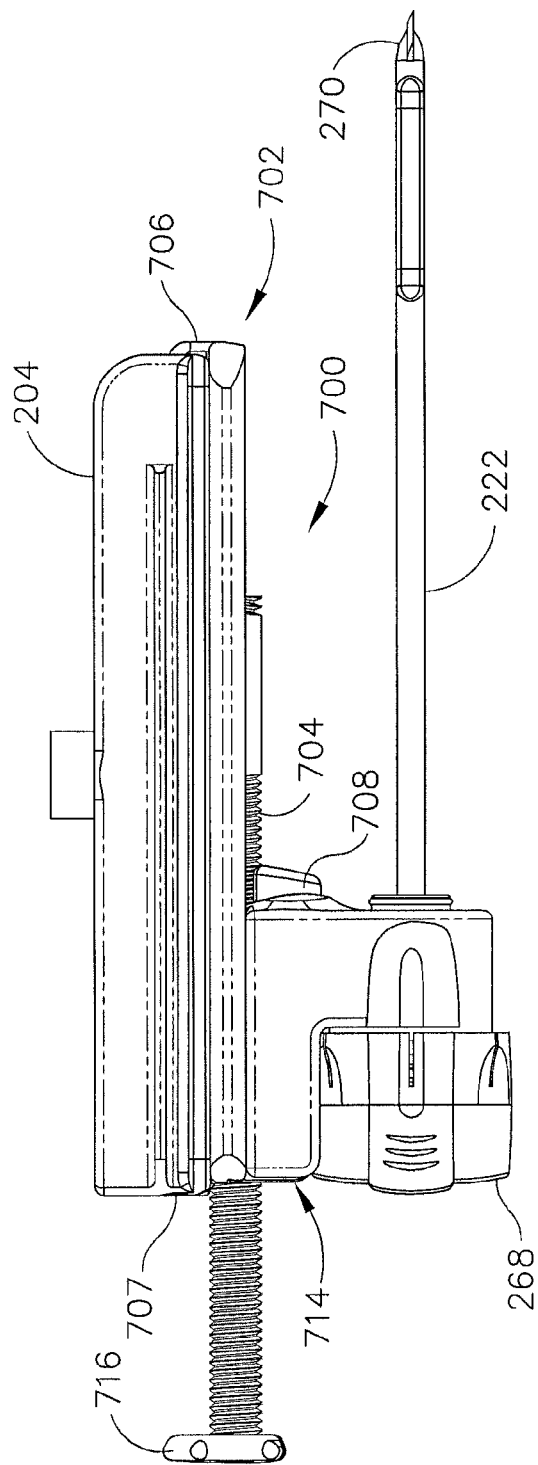
FIG. 14A is a top view of the telescoping depth guidance assembly of FIG. 14 mounted in a targeting rail of the MRI biopsy system of FIG. 1.

In FIGS. 14-20, a telescoping depth guidance assembly 700 for the MRI biopsy system 10 of FIG. 1 includes a depth stop second rail 702, particularly including a depth stop screw 704 in sliding engagement to an intermediate telescoping rail 706. The latter slidingly engages the primary targeting rail 204 (FIG. 14A) prior to the sleeve 222 and obturator 268 piercing tissue even with a most distal depth setting. At full insertion (FIG. 14A), a proximal lock 707 (FIG. 14) on the intermediate telescoping rail 706 engages the primary targeting rail 204. Rough adjustment of the depth setting is made by depressing a rough adjust button 708 on a distal side of a sleeve block 710, which disengages the sleeve block 710 from worm gear engagement to the depth stop screw 704. A ratchet mechanism formed between the sleeve block 710 and the intermediate telescoping rail 706 prevents the sleeve block 710 from being retracted unless a back button 714 is depressed.

Figure 15:
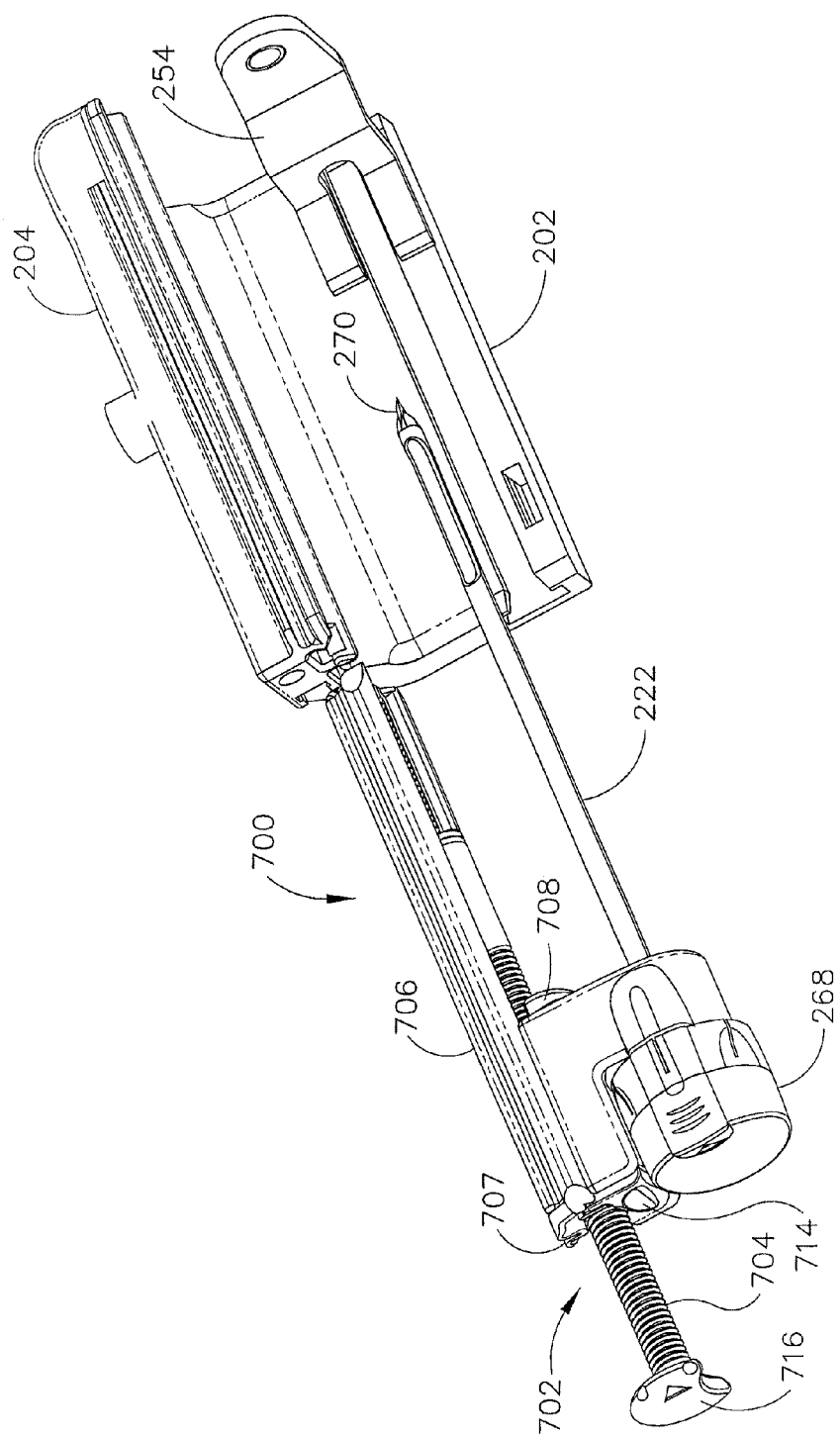
FIG. 15 is a top, proximal and right perspective view of the telescoping depth guidance assembly of FIG. 14 detached from a targeting rail and cradle.
Figure 15A:
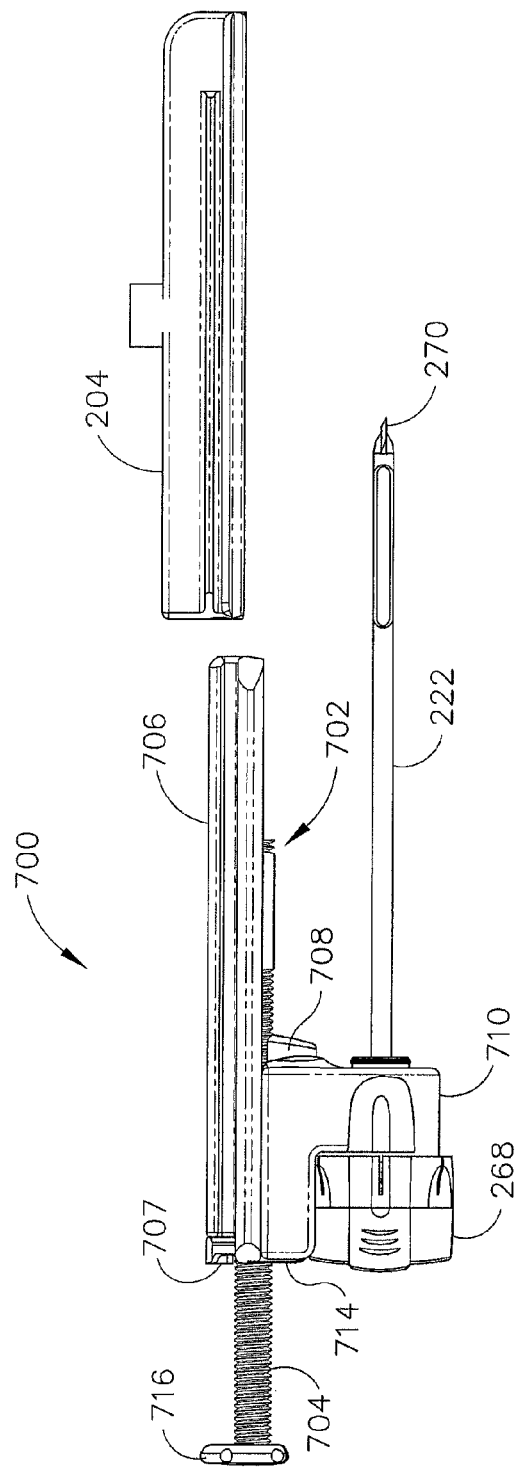
FIG. 15A is a top view of the telescoping depth guidance assembly and targeting rail of FIG. 15.
Figure 16:
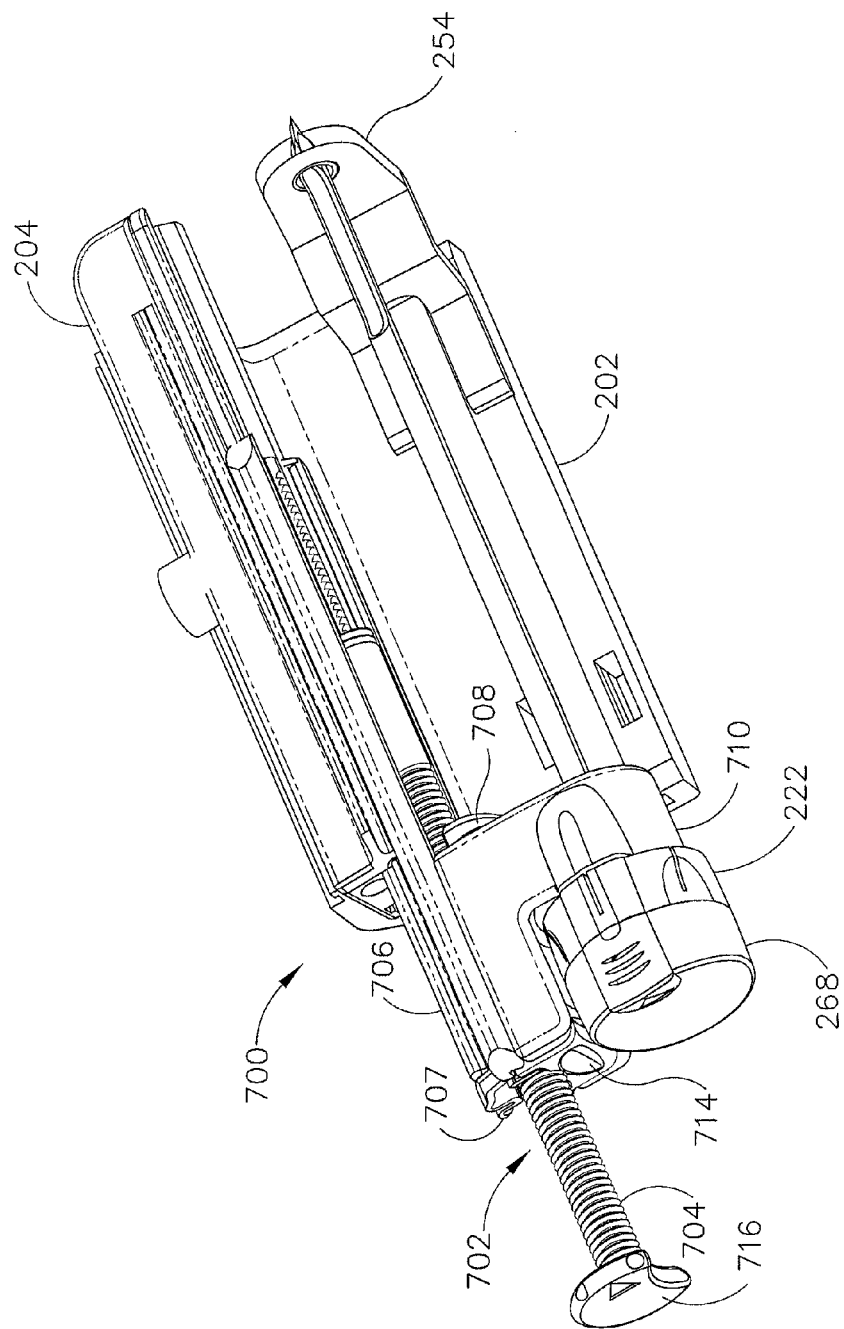
FIG. 16 is a top, proximal and right perspective view of the telescoping depth guidance assembly of FIG. 14 being guided by the targeting rail as the sleeve passes through a monocle on the cradle.
Figure 16A:
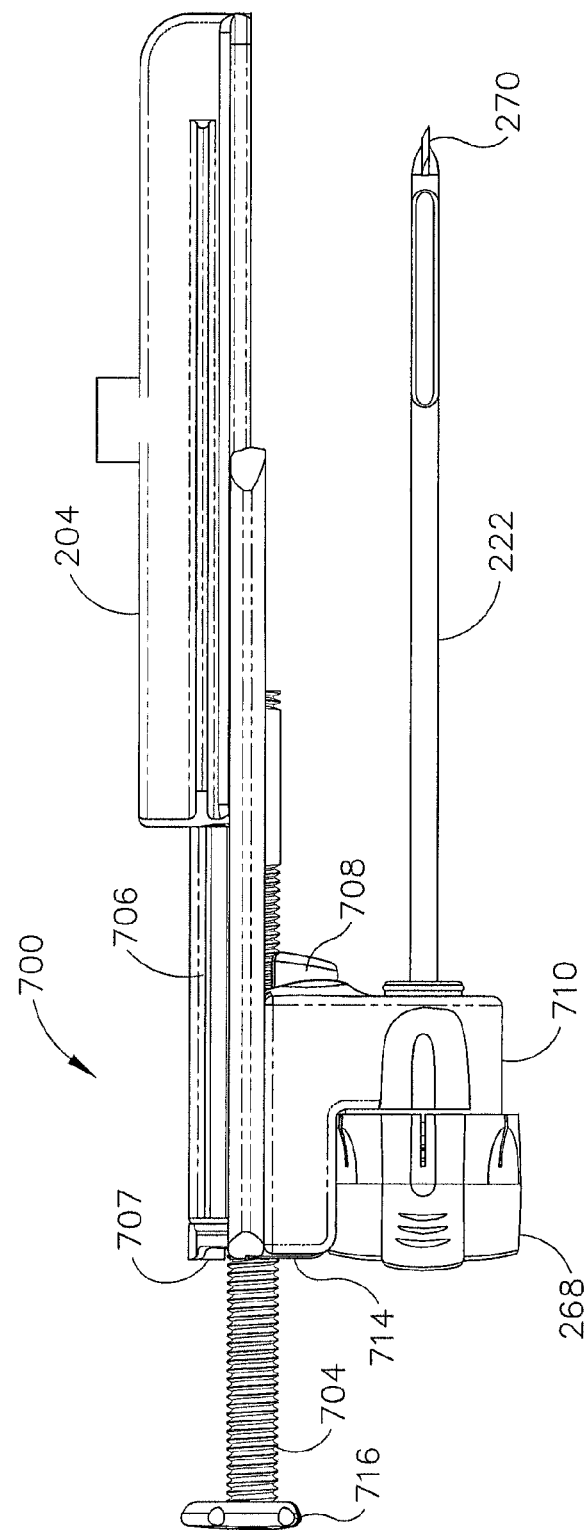
FIG. 16A is a top view of the telescoping depth guidance assembly of FIG. 16.
Figure 17:
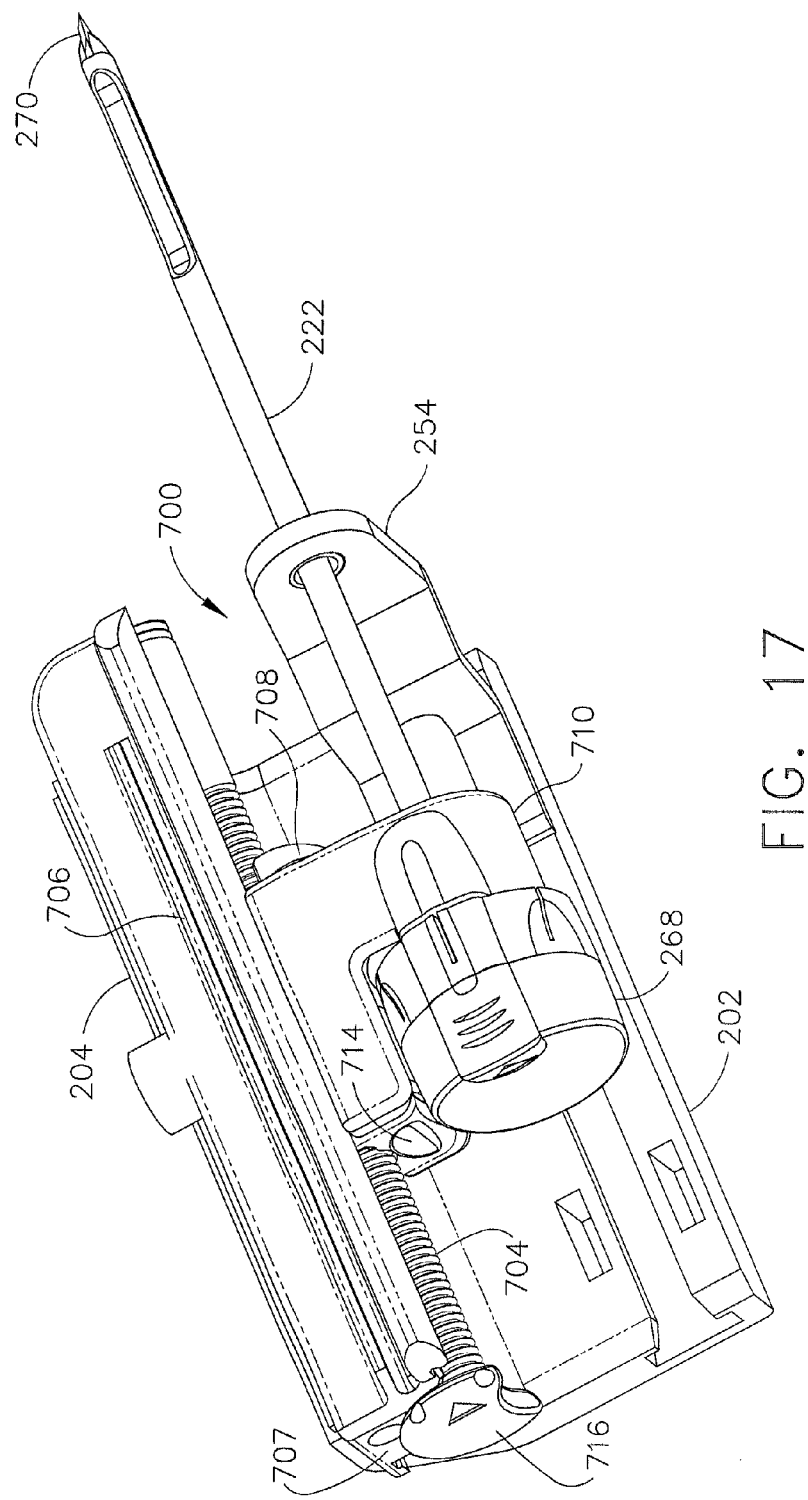
FIG. 17 is a top, proximal and right perspective view of the telescoping depth guidance assembly of FIG. 16 after reaching a first targeted depth.
Figure 17A:
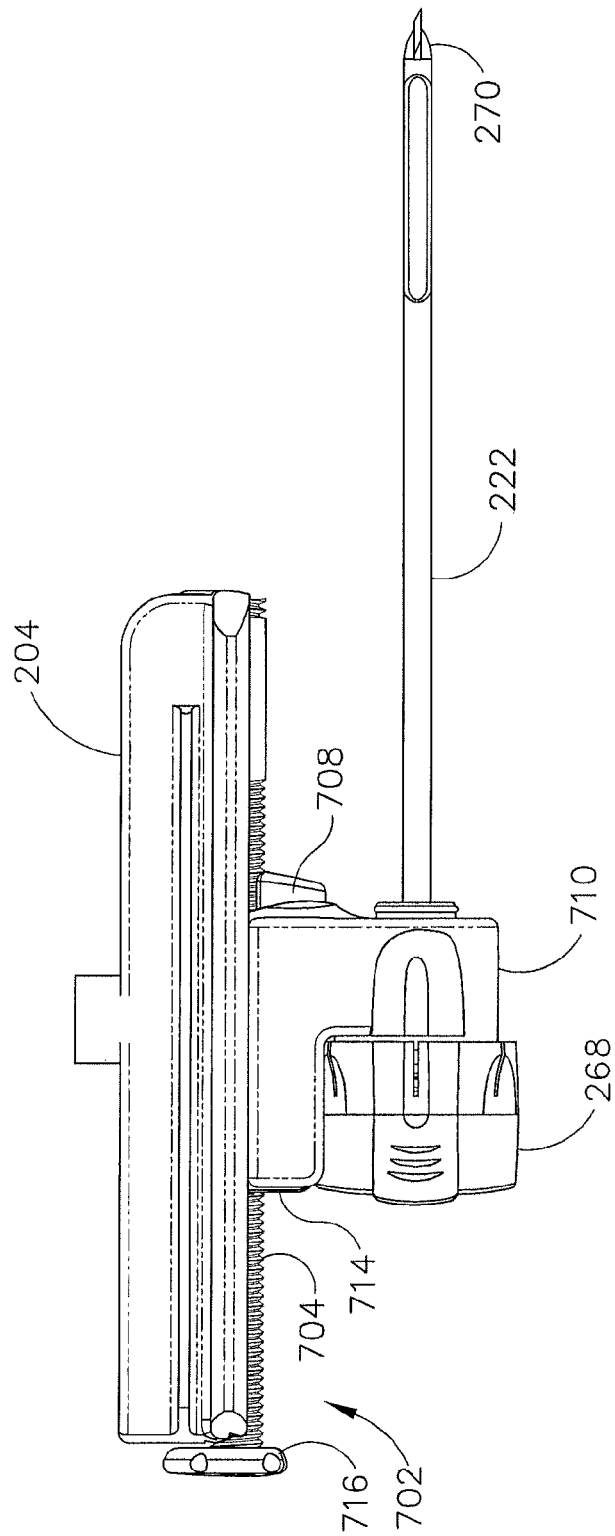
FIG. 17A is a top view of the telescoping guidance assembly of FIG. 17.
Figure 19:
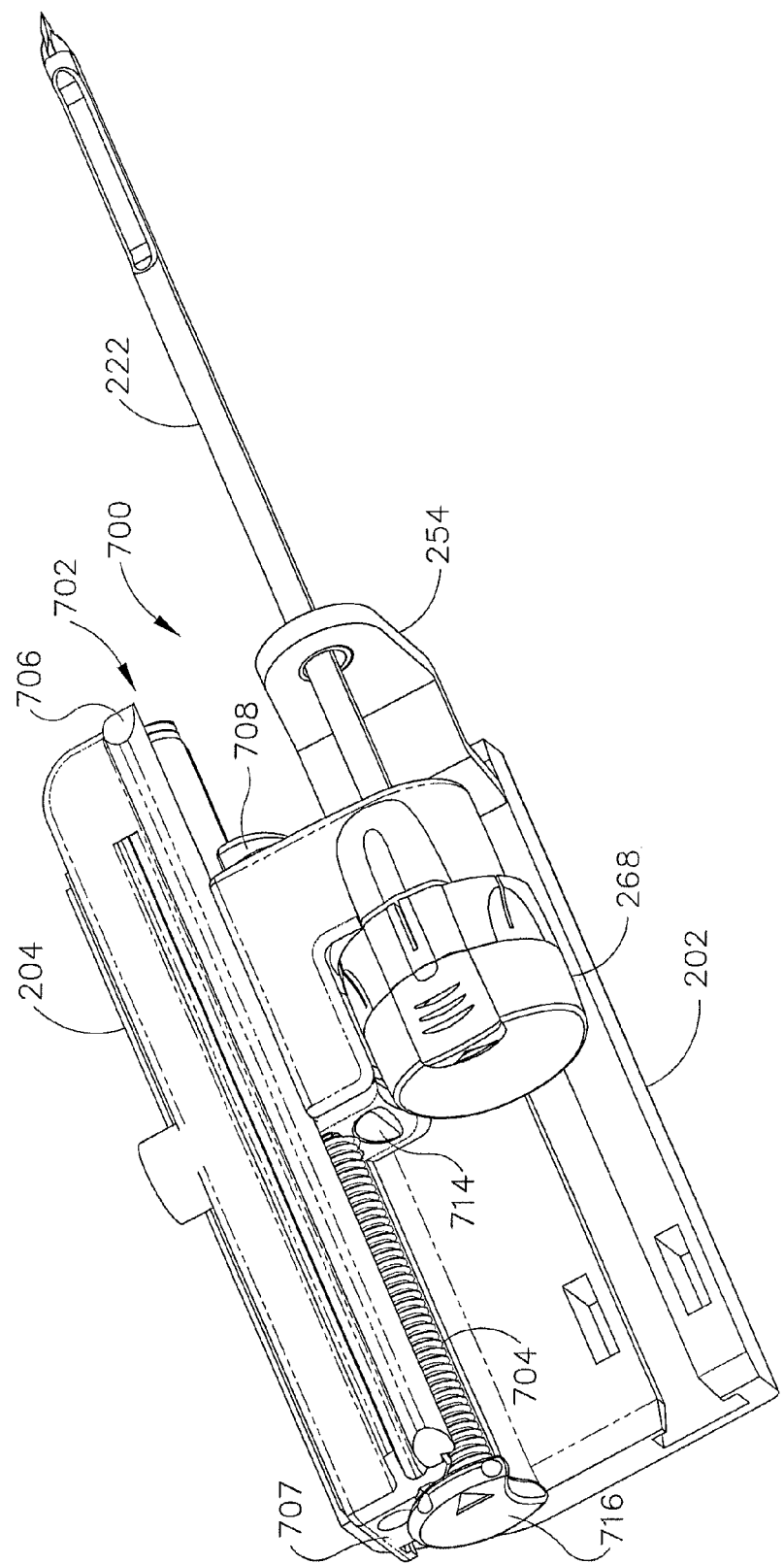
FIG. 19 is a top, proximal and right perspective view of the telescoping depth guidance assembly of FIG. 18 after distally inserting to the adjusted depth.
Figure 20:
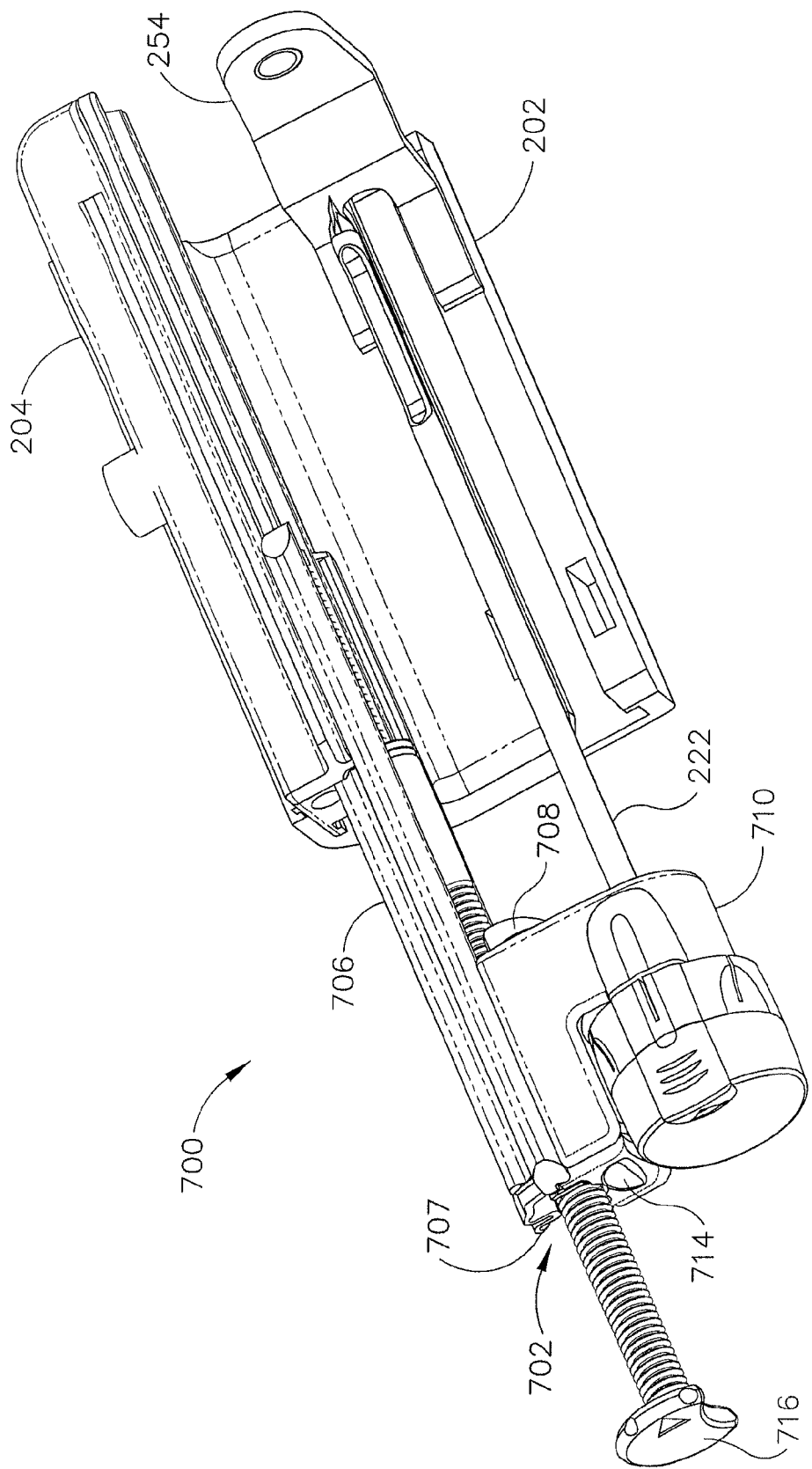
FIG. 20 is a top, proximal and right perspective view of the telescoping depth guidance assembly of FIG. 19 after depressing a proximal lock release and partially extracting the depth guidance assembly from the targeting rail and cradle.
Figure 23A:
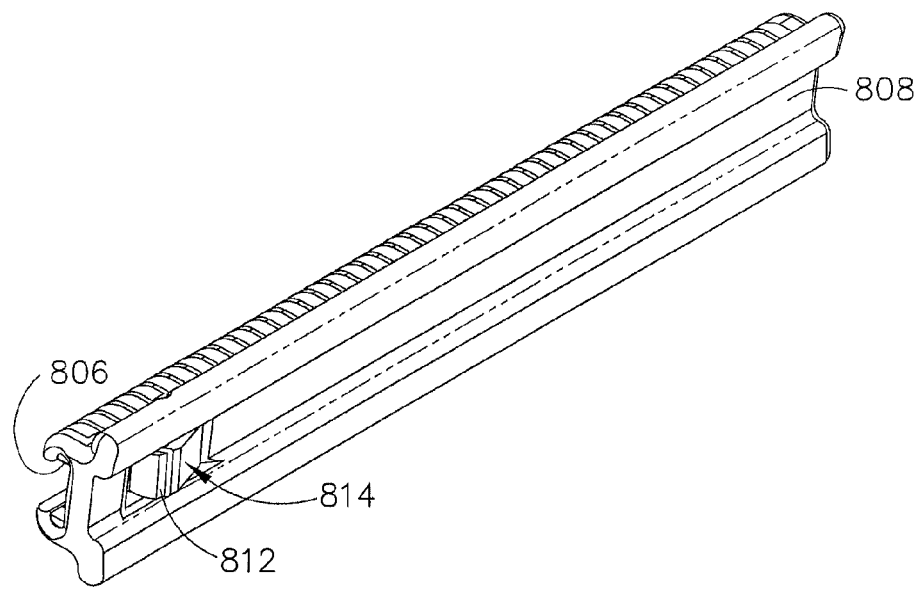
FIG. 23A is a perspective view of the alternative intermediate telescoping rail of FIG. 22, with a pawl in a first position.

In use, in FIGS. 15, 15A, the telescoping depth guide assembly 700 is advanced toward the cradle 202 and primary targeting rail 204. In FIGS. 16, 16A, the intermediate telescoping rail 706 is thus guided before the piercing tip 270 passes through the monocle 254 to pierce tissue until the proximal lock 707. In FIGS. 17, 17A, a rear depth stop tab 716 on the depth stop screw 704 is advanced until at its distal-most position, thereby distally advancing the sleeve block 710, sleeve 222, and obturator 268 to a first depth position. In response to a desired adjustment after reimaging or to take a second biopsy at an adjusted position that is at a greater depth into the breast, the rear depth stop tab 716 is rotated counterclockwise (or clockwise if the screw thread is reversed when viewed from behind) as depicted in FIG. 18 to slightly retract the depth stop screw 704. The sleeve block 710, however, is engaged to the intermediate telescoping rail 706 and remains in place. In FIG. 19, the rear depth stop tab 716 is pressed, advancing the depth stop screw 704, sleeve lock 712, sleeve 222, and obturator 268 to a second depth. If the initial depth is too great, the proximal lock is depressed slightly and the sleeve block is pulled back. This exposes the screw 704, and it can be rotated to set the new, shallower depth. In FIG. 20, the telescoping depth guide assembly 700 is removed from the primary targeting rail 204 by depressing the proximal lock 707, which releases the intermediate telescoping rail 706.

Pawl Locking Telescoping Depth Guidance Assembly.

Figure 24:
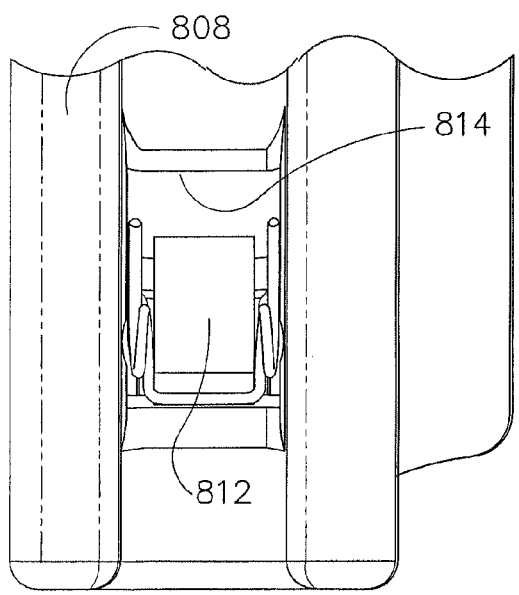
FIG. 24 is a right side view in elevation of a proximal portion of the intermediate telescoping rail of FIG. 23.
Figure 24A:
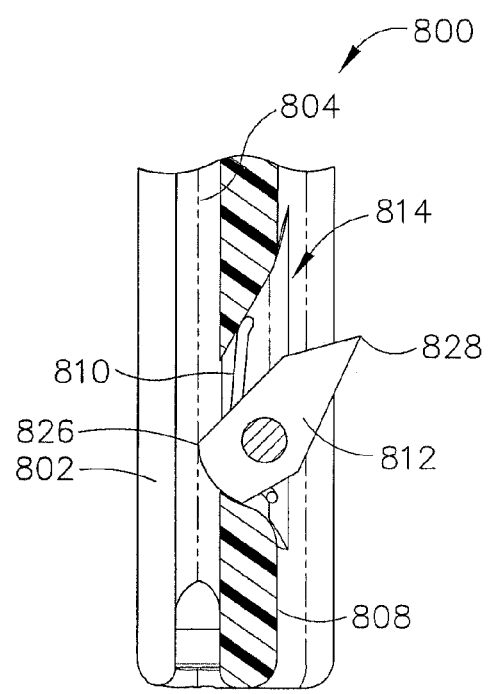
FIG. 24A is a top view of the proximal portion of the intermediate telescoping rail of FIG. 24 taken in cross section through the pawl, pawl recess of the primary targeting rail, and pawl aperture in the intermediate telescoping rail.
Figure 26:
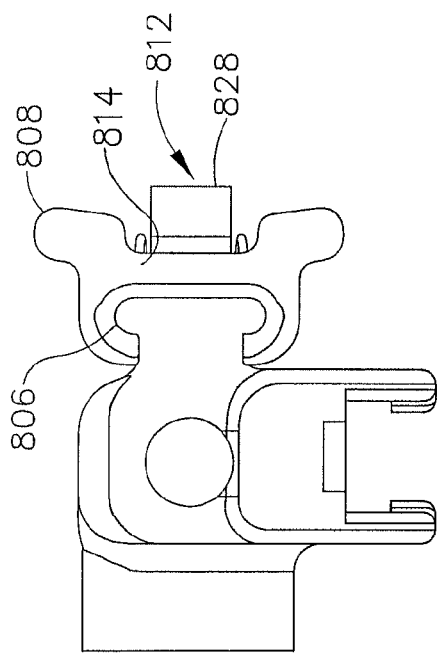
FIG. 26 is an aft view in elevation of the primary targeting rail and intermediate telescoping rail of FIG. 23.
Figure 27:
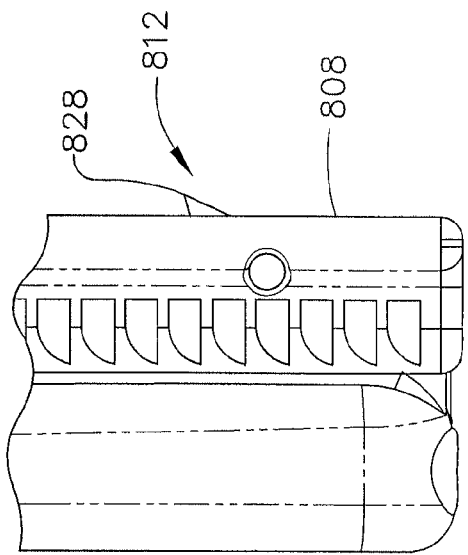
FIG. 27 is a left side view in elevation of the proximal portion of the intermediate telescoping rail.
Figure 25:
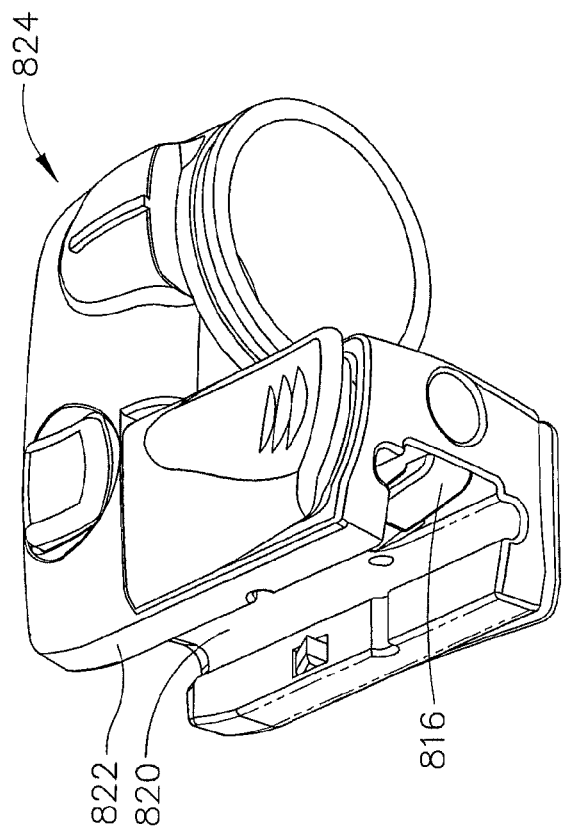
FIG. 25 is a perspective view of a sleeve block with locking tooth for the alternative intermediate telescoping rail of FIG. 22.

In FIGS. 21-27, an alternative telescoping depth guidance assembly 800 includes a primary targeting rail 802 (FIGS. 21, 23) that includes a guide tab surface 804 that slides within a leftward channel 806 (FIGS. 23, 23A) of an intermediate telescoping rail 808 (FIG. 22). The guide tab surface 804 has a proximally positioned pawl recess 810 that engages a spring biased pawl 812 that pivots within a laterally open aperture 814 (FIGS. 24, 24A) through a proximal end of the intermediate telescoping rail 808. A tooth 816 on a leftward engaging surface 820 of a gripping channel 822 of a sleeve mount 824 (FIGS. 25, 26) initially engages the pawl aperture 814, forcing the spring biased pawl 812 to rotate counterclockwise when viewed from above (FIG. 23A). As the intermediate telescoping rail 808 is slid distally onto the guide tab surface 804, a catch tip 826 (FIG. 24A) of the spring biased pawl 812 is urged into the pawl recess 810 preventing proximal retraction. Constraints on the proximal end of the leftward channel 806 of the intermediate telescoping rail 808 prevent further distal movement. A rightward distal tip 828 of the pawl 812 is rotated clockwise when viewed from the top disengaging the tooth 816 from the pawl aperture 814 allowing the sleeve mount 824 to slide distally over the intermediate telescoping rail 808 to the desired depth. Upon completion, retraction of the sleeve mount 824 causes the tooth 816 to abut the rightward distal tip 828 of the pawl 812, urging further clockwise rotation when viewed from above, disengaging the catch tip 826 from the pawl recess 810 and positioning the pawl 812 as depicted in FIG. 22 whereupon sleeve mount 824 binds to the unlocked intermediate telescoping rail 808 and draws both off of the primary targeting rail 802.

Laterally Guided Biopsy Cassette.

The above-described versions of the MRI biopsy system 10 advantageously enable remotely setting of a depth stop prior to engaging a biopsy device 14 with a localization fixture 16 to penetrate tissue. It would be desirable that the various components be assembled in a fashion that reduces separate sterile packaging, reduces the likelihood of damage due to contact with the sharp penetrating tip of a sleeve or obturator, and simplifies assembly and use. To that end, a dispensing housing partially enshrouds a penetrating member (e.g., detachable probe, close ended sleeve, open ended sleeve with penetrating obturator) while allowing access to a depth stop for presetting a desired depth of penetration. A dispensing actuator (e.g., plunger) is thereafter employed to effect engagement and penetration with the simultaneous removal of the dispensing housing from the penetrating member.

In FIGS. 28, 28A-C, 29A-29F, the dispensing housing is depicted as a laterally guided biopsy cassette 900 that integrates a glide sleeve 902 that acts as an intermediate telescoping rail to mount to a primary targeting rail 802 (FIG. 21). The glide sleeve 902 also encompasses a glide plunger 904 that in turn encompasses the tissue penetrating components (i.e., a sleeve 906 and an obturator 908) as a preassembled unit. In particular, the glide plunger 904 includes a proximal plunge handle 910 attached to a plunge tube (or arm) 912 having an inner longitudinal slot 914 (FIGS. 28, 28C) along a left side of the plunge tube 912 with a distal end of the longitudinal slot 914 communicating with a distal open end 916 of the plunge tube 912. The glide sleeve 902 has an outer longitudinal slot 918 with edges sized and contoured to engage the primary targeting rail 802 along a left side thereof registered to the inner longitudinal slot 914, with the outer longitudinal slot 918 having a distal end communicating with a open distal end 920 of the glide sleeve 902. A glide sleeve finger 922 is attached just proximal to the outer longitudinal slot 918 of the glide sleeve 902 and extends distally down a large portion of its length. A proximal portion of the glide sleeve finger 922 thickens inwardly abruptly to form a glide sleeve knuckle 923.

With particular reference to FIGS. 28, 28A, 28B, a longitudinally positionable plunger arm, depicted as a finger grasp 924, has distally projecting upper and lower flanges 926, 928 with respective upper and lower outwardly projecting obturator release buttons 930, 932 that slide in upper and lower longitudinal slots 934, 936 in the plunge tube 912. Proximal ends of each flange 926, 928 curl inward and back distally forming upper and lower spring ends 938, 940 attached to a finger grasp base 942, thereby exerting an outward bias on the flanges 926, 928. The flanges 926, 928 grip an obturator hub 944 of the obturator 908. A sleeve mount, depicted as an obturator guide 946, includes a cylindrical portion 948 that encompasses a sleeve hub 950 of the sleeve 906. Upper and lower guide arms 952, 954 (FIGS. 28, 28C) engage the outer longitudinal slot 918 and pass to either side of the glide sleeve finger 922. A depth stop ring 956 is initially proximally positioned on the plunge tube 912 next to the glide handle 910.

Figure 29D:
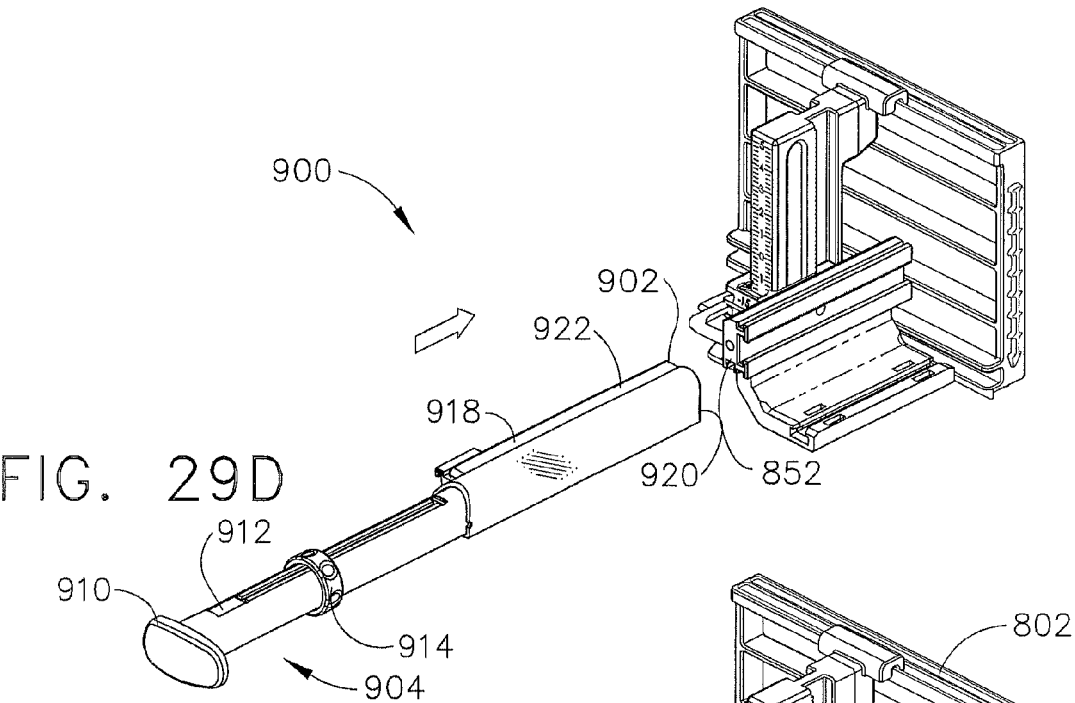
FIG. 29D is a perspective view of the laterally guided biopsy cassette of FIG. 29C as the glide sleeve and an obturator guide are engaged to a targeting rail of a localization fixture.
Figure 29E:
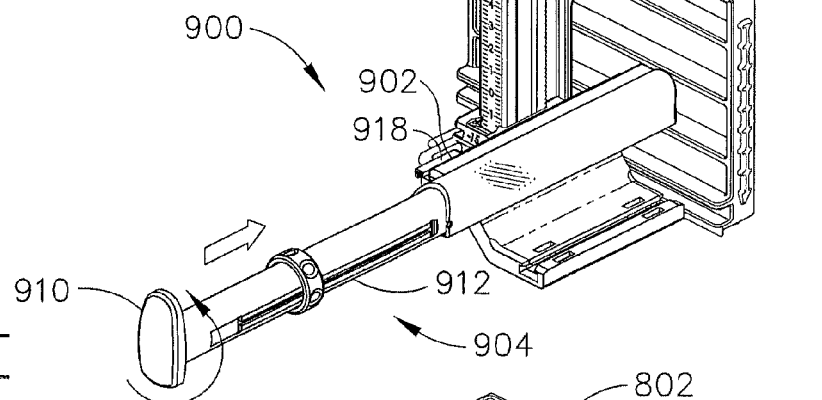
FIG. 29E is a perspective view of the plunger tube being unlocked from the glide sleeve.
Figure 29F:
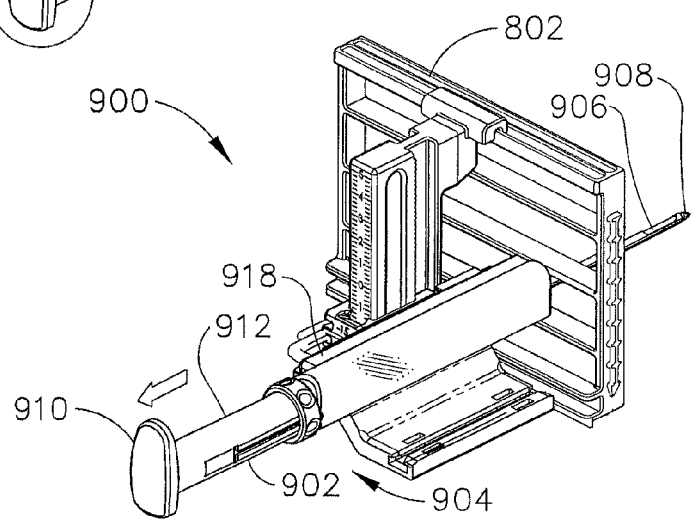
FIG. 29F is a perspective view of the plunger tube being advanced into the glide sleeve, causing penetration of the sleeve and obturator, allowing thereafter retraction of the glide sleeve from the targeting rail.

In use, in FIG. 29A, the laterally guided biopsy cassette 900 is in its preassembled state as removed from packaging for use. The glide sleeve 902 is to be advanced distally, as depicted by arrow 958, resulting in the telescoped state of FIG. 29B. Then the upper and lower outwardly projecting obturator release buttons 930, 932 are depressed to release from a proximal position and are slid forward distally until locked at a distal position as depicted in FIG. 29C. Thereby, the finger grasp 942 advances the obturator 908, obturator guide 946, and sleeve 906 out of the plunger tube 912 and into the advanced glide sleeve 902. In FIG. 29D, the depth stop ring 956 has been advanced along the plunge tube 912 with reference to measurement indicia thereon to a desired depth. Then, the laterally guided biopsy cassette 900 is engaged to a primary targeting rail 802. Specifically, the glide sleeve finger 922 slides therein until the glide sleeve knuckle 923 is reached. In FIG. 29E, the plunge handle 910 is rotated counterclockwise 90 degrees when viewed proximally. Thereby, the finger grasp 942 is also rotated by the plunge tube 912 until aligned with the outer longitudinal slot 918 of the glide sleeve 902 to unlock the glide plunger 904. In FIG. 29F, the glide plunger 904 is thus distally advanced into the glide sleeve 902. The obturator guide 946 is advanced so that its upper and lower flanges 926, 928 engage the primary targeting rail 802. The sleeve 906 and obturator 908 penetrate tissue until the depth stop ring 956 encounters the glide sleeve 902 preventing further advancement.

Cassette Deployed Second Rail Sleeve Mount with Rough Adjust and Release Buttons.

In FIGS. 30A-30F, a biopsy cassette 1000 has a transparent glide sleeve 1002 that holds the depth guidance assembly 600 of FIGS. 11-13. In FIG. 30A, a right-side slot 1005 runs down the length of a plunger tube 1004 with a protruding slide control 1006 at a proximal position. Coupled to the slide control 1006 is an obturator 1008 that is retracted into the plunger tube 1004 so as to protect its piercing tip from inadvertent contact. Thus, in FIG. 30B, the slide control 1006 acts as a longitudinally positionable plunger arm that has been distally advanced inserting the obturator 1008 into the sleeve 222. In addition, the depth may be preset on the depth guidance assembly 600 through use of the rough adjust button 608 and fine tuning screw handle 660 that are exposed by the transparent glide sleeve 1002. In FIG. 30C, the biopsy cassette 1000 is aligned to the primary targeting rail 802. In FIG. 30D, the biopsy cassette 1000 has advanced until the depth guidance assembly 600 is fully engaged to the primary targeting rail 802. In FIG. 30E, the biopsy cassette 1000 is retracted, leaving the depth guidance assembly 600 in place.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, other imaging modalities may benefit from aspects of the present invention. As another example, a fiduciary marker separate from the lateral plate may be positioned to a specific point on the exterior of the patient's breast as part of a guidance assembly.

As an example, while the illustrative versions incorporate positioning and penetration guidance along Cartesian X-Y-Z coordinates, it should be appreciated that applications consistent with the present invention may utilize other adjustment schemes such as spherical, cylindrical or other coordinate systems. It should be noted that various versions described above allowed for rotation of the depth guidance member such that the axis of penetration was not solely in the Z-axis, orthogonal to the X-Y axis defined by the localization fixture. This capability to adjust the angle of penetration may be desirable in certain instances to penetrate into the patient to minimize tissue damage (e.g., minimize the length of the penetrated tissue), to obscure any scarring of the skin, to avoid certain tissues such as the chest wall, etc As another example, other types of biopsy devices may advantageously be guided during penetration. In U.S. patent application Ser. No. 11/025,556 filed on 29 Dec. 2004, entitled "CORE SAMPLING BIOPSY DEVIDE WITH SHORT COUPLED MRI-COMPATIBLE DRIVER" to John A. Hibner, et al., the disclosure of which is hereby incorporated by reference in its entirety, both a long-stroke and a short-stroke core biopsy are described.

As another example, while many desirable features enable and enhance use in MRI suite, applications consistent with the present invention may be employed with other imaging modalities (e.g., ultrasonic, CT, etc.).

What is claimed is:

1. An apparatus for use with a biopsy device in a medical procedure, comprising:
   a. a first guide element extending longitudinally along an axis that is parallel to and offset relative to a selected axis of penetration into a patient;
   b. a mount movingly engageable to the guide element and operably configured to support a probe portion of the biopsy device, wherein the probe portion of the biopsy device comprises a penetrating portion; and
   c. a depth limiting member slidingly engageable with the guide element, wherein the depth limiting member is movable relative to the guide element along an axis that is parallel to the selected axis of penetration, the depth limiting member including a receptacle defining an opening aligned with the axis of penetration,
      i. wherein the receptacle is operably configured to contact a selected one of the mount or a proximal end of the penetrating portion of the biopsy device to arrest the penetrating portion of the biopsy device at a predetermined depth of insertion, and
      ii. wherein the receptacle is operably configured to guide a distal end of the penetrating portion of the biopsy device along the selected axis of penetration as the penetrating portion is inserted through the opening of the receptacle.

2. The apparatus of claim 1, wherein the depth limiting member selectively attaches to the guide element corresponding to the predetermined depth of insertion.

3. The apparatus of claim 1, wherein the mount comprises a holster coupled with the probe portion of the biopsy device.

4. The apparatus of claim 2, wherein the mount engages the proximal end of the penetrating portion, the depth limiting member registered to abut the mount to arrest movement thereof.

5. The apparatus of claim 4, further comprising a locking mechanism operably configured to resist retraction of the mount from the guide element.

6. The apparatus of claim 5, wherein the locking mechanism comprises a latch engageable between the mount and the depth limiting member.

7. The apparatus of claim 1, further comprising a cradle coupled to the guide element and extending laterally and vertically offset from the axis of penetration.

8. The apparatus of claim 7, wherein the cradle includes a biopsy guide vertically aligned with the axis of penetration and operably configured to movably engage a handle portion of the biopsy device.

9. The apparatus of claim 8, wherein the cradle is vertically aligned below the axis of penetration.

10. The apparatus of claim 1, further comprising a pedestal operatively configured to position the guide element parallel to a desired axis of penetration into a patient.

11. The apparatus of claim 10, wherein the pedestal and guide element include symmetrical engagement features enabling positioning of the guide element on either lateral side of the pedestal.

12. The apparatus of claim 11, wherein the biopsy device further comprises a cutting tube and a cutter mechanism operably configured to rotate and translate the cutting tube along the penetrating portion, the pedestal and guide element operably configured to position and align a distal tip of the penetrating portion of the biopsy device within 5 mm of a desired insertion point.

13. The apparatus of claim 12, wherein the pedestal and guide element are operably configured to position and align a distal tip of the penetrating portion of the biopsy device within 2 mm of a desired insertion point.

14. The apparatus of claim 1, further comprising a monocle coupled to a distal portion of the guide element, the monocle proximate to the patient and including a reticule aligned with the axis of penetration.

15. The apparatus of claim 1, further comprising a second guide element movably engageable to the first guide element, the second guide element including the mount adjustably positioned thereon and including the depth limiting member positioned to adjustably arrest the movable engagement between the second guide element and the mount.

16. The apparatus of claim 15, wherein the movable engagement between the first and second element is operably sized to initiate engagement prior to the piercing portion of the biopsy device encountering an insertion point on the patient.

17. The apparatus of claim 15, wherein the first guide element includes a first track, the second guide element further comprises:
    a rail operably configured to adjustably position the mount along its length parallel to the axis of penetration; and
    a second track surface registered to slidingly mate with the first track of the first guide element.

18. The apparatus of claim 17, wherein the mount includes an engaging knuckle operatively configured to selectively grip the rail of the second guide element to set a coarse depth adjustment.

19. The apparatus of claim 17, wherein the second guide element includes a rail retractably attached to the second track surface.

20. The apparatus of claim 17, wherein a depth measurement scale is positioned on a selected one of the first and second guide elements with a current depth position referenced by the other of the first and second guide elements.

21. The apparatus of claim 20, wherein the depth measurement scale comprises a measurement scale corresponding to a piercing member of a selected length.

22. The apparatus of claim 1, further comprising a biopsy holder comprising a glide sleeve encompassing the mount and the depth limiting member and distally open for insertion onto the first guide element, and comprising a plunger positioned to retract the glide sleeve off of the mount and the depth limiting member after engagement to the first guide element.

23. The apparatus of claim 22, wherein the penetrating portion of the biopsy device comprises a probe and an obturator, the plunger of the biopsy holder further comprises a distally open plunger tube containing a longitudinally positionable plunger arm having a proximal position and distal position wherein the plunger tube is sized to receive at least a selected one of the probe and the obturator.

24. The apparatus of claim 1, further comprising a piercing member attached to the mount.

25. The apparatus of claim 24, wherein the piercing member comprises a sleeve comprising an elongate hollow tube having a side aperture proximate to a distal end and a sleeve hub engaged to the mount, the sleeve sized to receive a selected one of an obturator and the probe of the biopsy device.

26. The apparatus of claim 25, wherein the sleeve includes an open distal end, the obturator including a piercing tip extending from the sleeve, the obturator further comprising a solid shaft with a recess positioned to coincide with the side aperture of the sleeve, the obturator including a locking mechanism attachable to the sleeve hub to align the recess with the side aperture.

27. The apparatus of claim 24, wherein the piercing member includes a lumen in fluid communicating between a distal opening and a proximal opening.

28. The apparatus of claim 27, wherein the piercing member comprises a sleeve and an obturator including a hollow shaft defining at least a portion of the lumen.

29. The apparatus of claim 27, wherein the proximal opening of the lumen comprises a selected one of a group consisting of a luege fitting, hose fitting and a syringe fitting.

* * * * *